(12) United States Patent
Ahuja et al.

(10) Patent No.: US 10,167,513 B2
(45) Date of Patent: Jan. 1, 2019

(54) COMPOSITIONS AND METHODS FOR DETECTING A NEOPLASIA

(75) Inventors: Nita Ahuja, Lutherville, MD (US); Stephen Baylin, Baltimore, MD (US); James G. Herman, Lutherville, MD (US); Jeff Wang, Timonium, MD (US); Vasudev Bailey, Baltimore, MD (US); Mi J. Yi, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 163 days.

(21) Appl. No.: 13/699,452

(22) PCT Filed: May 25, 2011

(86) PCT No.: PCT/US2011/037926
§ 371 (c)(1),
(2), (4) Date: Jul. 3, 2013

(87) PCT Pub. No.: WO2011/150075
PCT Pub. Date: Dec. 1, 2011

(65) Prior Publication Data
US 2013/0288241 A1    Oct. 31, 2013

Related U.S. Application Data

(60) Provisional application No. 61/348,010, filed on May 25, 2010.

(51) Int. Cl.
*C07H 21/04* (2006.01)
*C12Q 1/6886* (2018.01)
*G01N 33/574* (2006.01)
*C12Q 1/68* (2018.01)

(52) U.S. Cl.
CPC ..... *C12Q 1/6886* (2013.01); *G01N 33/57407* (2013.01); *G01N 33/57419* (2013.01); *G01N 33/57423* (2013.01); *G01N 33/57438* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 7,112,404 | B2 * | 9/2006 | Laird | C12Q 1/6858 435/6.14 |
| 2010/0233707 | A1 * | 9/2010 | Buckingham | 435/6 |

OTHER PUBLICATIONS

Gore et al. (Cancer Res, vol. 66, No. 12, pp. 6361-6369, Jun. 15, 2006).*
Omura et al. (Cancer Biology & Therapy, vol. 7, No. 7, pp. 1146-1156, Jul. 1, 2008).*
Shames et al. (PLOS Medicine, vol. 3, No. 12, e486, Dec. 2006).*
Dunwell et al. (Epigenetics, vol. 4, No. 3, pp. 185-193, Apr. 2009).*
Morris et al. (Oncogene, vol. 29, No. 14, pp. 2104-2117, Apr. 8, 2010).*
Choi et al. (Cancer Genetics and Cytogenetics, vol. 187, pp. 80-84, 2008).*
Ahlquist et al. (Molecular Cancer, vol. 7, No. 94, pp. 1-11, Dec. 2008).*
Lind et al (Cellular Oncology, vol. 28, pp. 259-272, 2006).*
Shames, David S et al: "A genome-wide screen for promoter methylation in lung cancer identifies novel methylation markers for multiple malignancies", PLOS Medicine, Public Library of Science, US, vol. 3, No. 12, Dec. 1, 2006, pp. 2245-2246, 2258-2260.
Choi J E et al: "Aberrant methylation of ADAMTS1 in non-small cell lung cancer", Cancer Genetics ADN Cytogenetics, Elsevier Science Publishing, New York, NY, US, vol. 187, No. 2, Dec. 1, 2008, pp. 80-84.
Philip J. Johnson et al: "Plasma Nucleic Acids in the Diagnosis and Management of Malignant Disease", Clinical Chemistry, vol. 48, No. 8, Aug. 1, 2002, pp. 1186-1193.
Esteller M: "Relevance of DNA methylation in the management of cancer", Lancet Oncology, Lancet Publishing Group, London, GB, vol. 4, No. 6, Jun. 1, 2003, pp. 351-358.
G Strathdee et al: "Aberrant DNA methylation in cancer: potential clinical interventions", Expert Reviews in Molecular Medicine, vol. 4, Mar. 1, 2002, pp. 1-17.
Seo D et al: "Genomic medicine: bringing biomarkers to clinical medicine", Current Opinion in Chemical Biology, Current Biology Ltd, London, GB, vol. 9, No. 4, Aug. 1, 2005, pp. 381-386.
Extended European search report for corresponding European Application No. 11787338.0, dated Nov. 13, 2013, 13 pages.
Shames et al., "A genome-wide screen for promoter methylation in lung cancer identifies novel methylation markers for multiple malignancies", PLoS Medicine, vol. 3(12): e486 (Dec. 2006).
Choi et al., "Aberrant methylation of ADAMTS1 in non-small cell lung cancer", Cancer Genetics and Cytogenetics, vol. 187(2); pp. 80-84 (Dec. 2008).
Johnson et al., "Plasma nucleic acids in the diagnosis and management of malignant disease", Clinical Chemistry, vol. 48(8), pp. 1186-1193 (Aug. 2002).
Ahlquist et al., "Gene methylation profiles of normal mucosa, and benign and malignant colorectal tumors identify early onset markers" Molecular Cancer, vol. 7: 94 (Dec. 31, 2008).
Morris et al, "Identification of candidate tumour suppressor genes frequesntly methylated in renal cell carcinoma", Oncogene, Apr. 8, 2010; 29(14): 2104-2117.
International Searc Report for PCT/US2011/037926 dated Feb. 9, 2012.

* cited by examiner

*Primary Examiner* — Jeanine A Goldberg
(74) *Attorney, Agent, or Firm* — Mintz Levin Cohn Ferris Glovsky and Popeo, P.C.; Peter F. Corless

(57) ABSTRACT

The invention provides compositions and methods for detecting a neoplasia (e.g., pancreatic cancer, lung cancer, colon cancer) in a subject sample (e.g., serum, blood, plasma, tissue). In particular embodiments, the invention provides methods for detecting BNC1 and ADAMTS1 promoter methylation in circulating DNA in serum.

8 Claims, 6 Drawing Sheets

Specification includes a Sequence Listing.

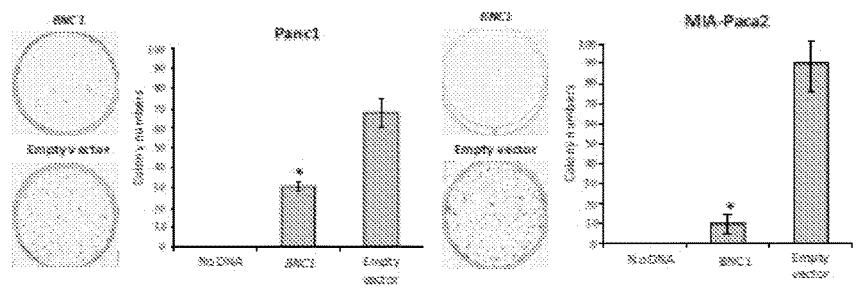
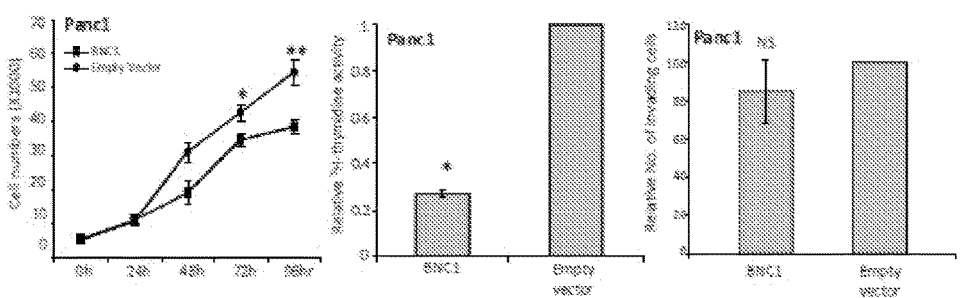
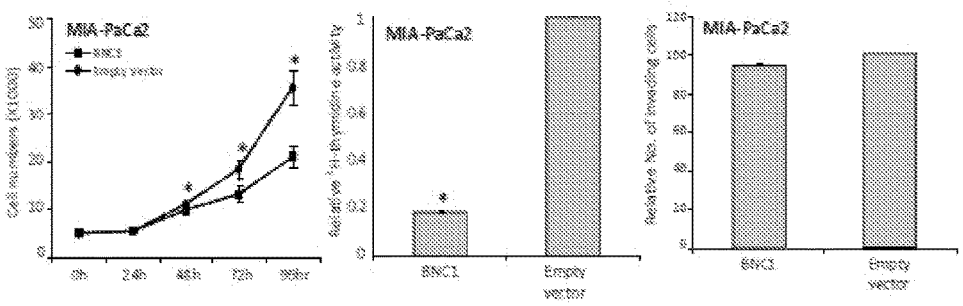
Figure 4A, 4B, and 4C

SEQUENCE LISTING

```
<160> NUMBER OF SEQ ID NOS: 44

<210> SEQ ID NO 1
<211> LENGTH: 4627
<212> TYPE: DNA
<213> ORGANISM: Homo sapiens

<400> SEQUENCE: 1
gcggcggggg cggccatcgt gctgcgcagc ctgggcgctt ggggagccgc ccacttcgcc      60
gggtcgcgcc ccgacggccg gagcgtggat gcggcggcgc ccgccgagcc ggggcggacg     120
cggggcggcc cgggcccggg agacgcgccg gcagccccgg caccgcagcg gtcgcaggat     180
ggccgaggct atcagctgta ctctgaactg tagttgccaa agtttcaaac ccgggaaaat     240
aaaccaccgt cagtgtgacc aatgcaagca tggatgggtg gcccacgctc taagtaagct     300
aaggatcccc cccatgtatc caacaagcca ggtggagatt gtccagtcca atgtagtgtt     360
tgatattagc agcctcatgc tctatgggac ccaggccatc cccgttcgcc taaaaatcct     420
actggaccgg ctcttcagtg tgttgaagca agatgaggtt ctccagatcc tccatgcctt     480
ggactggaca cttcaggatt atatccgtgg atacgtactg caggatgcat caggaaaggt     540
gttggatcac tggagcatca tgaccagtga ggaagaagtg gccaccttgc agcagttcct     600
tcgttttgga gagaccaaat ctatagttga actcatggca attcaagaga agaagagca      660 atccatcatc ataccacctt ccacagcaaa tgtagatatc agggctttca tcgagagctg     720
cagtcacagg agttctagcc tccccactcc tgtggacaaa ggaaacccca gcagtataca     780
cccctttgag aacctcataa gcaacatgac tttcatgctg cctttccagt tcttcaaccc     840
tctgcctcct gcactgatag ggtcattgcc cgaacaatat atgttggagc agggtcatga     900
ccaaagtcag gaccccaaac aggaagtcca tgggcccttc cctgacagca gcttcttaac     960
ttccagttcc acaccatttc aggttgaaaa agatcagtgt ttaaactgtc cggatgctat    1020
tactaaaaaa gaagacagca cccatttaag tgactccagc tcatacaaca ttgtcactaa    1080
gtttgaaagg acacagttat cccctgaggc caaagtgaag cctgagagga atagccttgg    1140
tacaaagaag ggccgggtgt tctgcactgc atgtgagaag accttctatg acaaaggcac    1200
cctcaaaatc cactacaatg ccgtccactt gaagatcaag cataagtgca ccatcgaagg    1260
gtgtaacatg gtgttcagct ccctaaggag ccggaatcgc catagcgcca accccaaccc    1320
tcggctgcac atgccaatga acagaaataa ccgggacaaa gacctcagga acagcctgaa    1380
cctggccagc tctgagaact acaagtgccc aggtttcaca gtgacgtccc cagactgtag    1440
gcctcctccc agctaccctg gttcaggaga ggattccaaa ggccaaccag ccttcccaaa    1500
cattgggcaa aatggtgtgc tttttcccaa cctaaagaca gtccagccag tccttccttt    1560
ctaccgcagt ccagccacgc ctgccgaggt agcaaacacg cctgggatac tcccttccct    1620
cccgctgttg tcctcttcaa tcccagaaca gctcattcta aacgaaatgc catttgatgc    1680
ccttcccaag aagaaatcca ggaagtccag tatgcctatc aaaatagaga aagaagctgt    1740
ggaaatagct aatgagaaaa gacacaacct cagctcagat gaagacatgc cctacaggt      1800 ggtcagtgaa gatgagcagg aggcctgcag tcctcagtca cacagagtat ctgaggagca    1860
```

```
gcatgtacag tcaggaggct tagggaagcc tttccctgaa ggggagaggc cctgccatcg    1920
tgaatcagta attgagtcca gtggagccat cagccaaacc cctgagcagg ccacacacaa    1980
ttcagagagg gagactgagc agacaccagc attgatcatg gtgccaaggg aggtcgagga    2040
tggtggccat gaacactact tcacacctgg gatggaaccc caagttcctt tttctgacta    2100
catggaactg cagcagcgcc tgctggctgg gggactcttc agtgctttgt ccaacagggg    2160
aatggctttt ccttgtcttg aagattctaa agaactggag cacgtgggtc agcatgcatt    2220
agcaaggcag atagaagaaa atcgcttcca gtgtgacatc tgcaagaaga cctttaaaaa    2280
tgcttgtagt gtgaaaattc atcacaagaa tatgcatgtc aaagaaatgc acacatgcac    2340
agtggagggc tgtaatgcta ccttttccctc ccgcaggagc agagacagac acagctcaaa    2400
cctaaacctc caccaaaaag cattgagcca ggaagcattg gagagtagtg aagatcattt    2460
ccgtgcagct taccttctga agatgtggc taaggaagcc tatcaggatg tggcttttac    2520
acagcaagcc tcccagacat ctgtcatctt caaaggaaca agtcgaatgg gcagtctggt    2580
ttacccaata acgcaagtcc acagtgccag cctggagagc tacaactctg gcccctttgag    2640 cgagggcacc atcctggatt tgagcactac ctcgagcatg aagtcagaga gtagcagcca    2700
ttcttcctgg gactctgacg gggtgagtga ggaaggcact gtgcttatgg aggacagtga    2760
tgggaactgt gaagggtcga gccttgtccc tggggaagat gagtacccca tctgtgtcct    2820
gatggagaag gctgaccaga gccttgctag cctgccttct gggttgccca taacctgtca    2880
tctctgccaa aagacataca gtaacaaagg gacctttagg gcccactaca aaactgtgca    2940
cctccggcag ctccacaaat gcaaagtacc aggctgcaac accatgtttt cgtctgttcg    3000
cagtcgaaac agacacagcc agaatcccaa cctgcacaaa agcctggcct catctccaag    3060
tcacctccag taacaagatg gcaaaccaag tatgctcaga taagcttttt tcataattca    3120
ggaataaagt agtccataga aatgtttctg tttcatatca tttggggcga gtcaggcaaa    3180
agtatttgat ttgactttat agttttccac agcacaatga gcaaaagaca aacctcgtgg    3240
gaagatgaca ctgggcagc ccttcctatt attttctta gcccaagagg tctttcactg    3300
atacaaggaa aacttgcaga aatgtgattt ttcccagatt tgtttacatg ttccctggga    3360
cagatccagg tctgcagatc gacaccagtg ggcccaggac ctgggggtgg ctttaaatga    3420
ggcttgcagt gttaaaggtc ttggataaga agggtcctgg ggaagaagac tctgtggaca    3480
agataccagt ccccaaaaca gcattttcag ttccttcttc aattagtttg aaatccagac    3540
ctgagtttgg aagactgatt ttttgagacc atccctgtgt ttggagtgga taattgtccc    3600 tccccctcagc cctgcaccag aggtctcata tgttacccca gggagttctc agaggattgg    3660
gttggcctct aacatgttcc ttgttaattc ttgttctgta acatgcattc aagaagctag    3720
gggaaaaata tctcatgcac ttaaataatg gtcttcaatt taatttaaaa atattttgac    3780
aatatttaat ttgtgcttat gtggtgtttg gtgtgagtgc agatattgca ctgtgtcacc    3840
tctggatctc tgctcagaag cagaacaagt gatgacctaa atgtcaaaat cactgctcgt    3900
tttcatttgg tgaacttcaa actctgttct ttttggtcac ctgtggaatg aatgcaagca    3960
tgattttggc aggaacattt gtacatattc tgccgtagat aatgtggttc tgatggttgt    4020
tgtgtatttt cagtatcact ggatccctca gtcttcaccg ttttataaac gtataagatt    4080
aggatgaact tttgaattta cttggtagga aaaaagtag gacattattg ccatattgta    4140
tgtcttaata tttaacttat tcggaaatat attccacact gttacataca ttttccatgg    4200
```

```
tagaaaggaa gttcagtcag tcctgtggaa tgaaaccatc tcctaaaatt cagcatttgc    4260
agcattctaa aagcctgtgt aggtacaagg acattgattt tgtattcaga attcaagtta    4320
actatctttt aaattcgtgg ttgatgtaag taataaaaaa cattcttaaa gttgagggtt    4380
ataagagaga ttatttctgt ggtctaaagg ttaaaaagcc aacaacctgt taccaattat    4440
ttcagctttt tttgttttaa taagtgtgac aacttaaaac ttgtttctat ttaaagtgaa    4500
atgtatcttt caactgttta gttacccagc tgtttaatat tccagtcttc ccaaagtgaa    4560
aagatttgta tacaaatgtt ttctatgatt taataaaaat atatggcaca ccaaaaaaaa    4620
aaaaaaa                                                              4627

<210> SEQ ID NO 2
<211> LENGTH: 1000
<212> TYPE: DNA
<213> ORGANISM: Homo sapiens

<400> SEQUENCE: 2
gtttcctttt caaggatccc caccagcagc aaggcaggtg aagaaactg agggaagagg      60 aagcaggacc cccgccgccc cccagtcta gcctttacag actccttta aggagctgaa     120 gaggttggga gaggcttgcc ctgccccggg gcagcagaaa cccggcgct gctgcagcag     180 ctgtgggcga tctccgtcag ctcctgggct ccaggatcct gcggcctcag ccctccgcg     240 tctactctcg gggccaccac ctccagttgg cttctccagg gcacttcatt tcattccgtc    300
cctagcatcc aataagacgc gaaaaactta atcccatttt acaactgaag ccactgaggc    360
ccagagagca aagccatttg tcctgggaaa gtggtcaagc tgggactttg actcttcaga    420
ccacccaagg gaagggtgt gtgtgtgtgt gtgtgtgtgt gtgcgtgtgc ggtgggggc      480 gcttgttttg agttcttaag aaaacctcct ggcgaccccc ttcttccaca tcccaagacg    540
ctcgtcccgc actttctcgg gaatgaggtt tctgcaggcg agggcggcgc tgccttcttc    600
ctccgcggca gtgagacccc gagggcgccc caggtagga ggggaggccg aatcatctcc     660
tgagaagagc gccagagaac ttcagagcgt ttcgcccttc cccgggagag gcaaacaccg    720
acacgtctgt gtcttttacc aacaagtgcc ttcaagcccg gcggggcag acacctccgc     780 gccggccgcc ggcgaggtct ccgcggtctg cgggggccac ggcctcgcct cagctgcgct    840
gatttagggc gttatccggt cccggggcgg gaggcggcct cccggggcgg gaagcagcgc    900
ccgcggcgtg gggcgaccgc gcggtgggcg gaggggcagg gggaggggcg gagaggcgtc    960
cccggggcgc aggggggcgg cgtgcgggca cacgcggtgc                         1000

<210> SEQ ID NO 3
<211> LENGTH: 200
<212> TYPE: DNA
<213> ORGANISM: Homo sapiens

<400> SEQUENCE: 3
gcggcggggg cggccatcgt gctgcgcagc ctgggcgctt ggggagccgc ccacttcgcc     60
gggtcgcgcc ccgacggccg gagcgtggat gcggcggcgc ccgccgagcc ggggcggacg    120
cggggcggcc cggccccggg agacgcgccg gcagccccgg caccgcagcg gtcgcaggat    180
ggccgaggta agcgcggcgc                                                200

<210> SEQ ID NO 4
<211> LENGTH: 4670
<212> TYPE: DNA
<213> ORGANISM: Homo sapiens
```

<400> SEQUENCE: 4

```
gcactcgctg gaaagcggct ccgagccagg ggctattgca aagccagggt gcgctaccgg        60
acggagaggg gagagccctg agcagagtga gcaacatcgc agccaaggcg gaggccgaag       120
aggggcgcca ggcaccaatc tccgcgttgc ctcagccccg gaggcgcccc agagcgcttc       180
ttgtcccagc agagccactc tgcctgcgcc tgcctctcag tgtctccaac tttgcgctgg       240
aagaaaaact tcccgcgcgc cggcagaact gcagcgcctc cttttagtga ctccgggagc       300
ttcggctgta gccggctctg cgcgcccttc caacgaataa tagaaattgt taattttaac       360
aatccagagc aggccaacga ggctttgctc tcccgacccg aactaaaggt ccctcgctcc       420
gtgcgctgct acgagcggtg tctcctgggg ctccaatgca gcgagctgtg cccgaggggt       480
tcggaaggcg caagctgggc agcgacatgg ggaacgcgga gcgggctccg gggtctcgga       540
gctttgggcc cgtacccacg ctgctgctgc tcgccgcggc gctactggcc gtgtcgacg        600
cactcgggcg cccctccgag gaggacgagg agctagtggt gccggagctg gagcgcgccc       660
cgggacacgg gaccacgcgc ctccgcctgc acgcctttga ccagcagctg gatctggagc       720
tgcgccccga cagcagcttt ttggcgcccg gcttcacgct ccagaacgtg gggcgcaaat       780
ccgggtccga gacgccgctt ccggaaaccg acctggcgca ctgcttctac tccggcaccg       840
tgaatggcga tccagctcg gctgccgccc tcagcctctg cgaggcgtg cgcggcgcct        900
tctacctgct gggggaggcg tatttcatcc agccgctgcc cgccgccagc gagcgcctcg       960
ccaccgccgc cccaggggag aagccgccgg caccactaca gttccacctc ctgcggcgga      1020
atcggcaggg cgacgtcggc ggcacgtgcg gggtcgtgga cgacgagccc cggccgactg      1080
ggaaagcgga gaccgaagac gaggacgaag ggactgaggg cgaggacgaa ggggctcagt      1140
ggtcgccgca ggacccggca ctgcaaggcg taggacagcc cacaggaact ggaagcataa      1200
gaaagaagcg atttgtgtcc agtcaccgct atgtggaaac catgcttgtg gcagaccagt      1260
cgatggcaga attccacggc agtggtctaa agcattacct tctcacgttg ttttcggtgg      1320
cagccagatt gtacaaacac cccagcattc gtaattcagt tagcctggtg gtggtgaaga      1380
tcttggtcat ccacgatgaa cagaaggggc cggaagtgac ctccaatgct gccctcactc      1440
tgcggaactt ttgcaactgg cagaagcagc acaacccacc cagtgaccgg gatgcagagc      1500
actatgacac agcaattctt ttcaccagac aggacttgtg tgggtccag acatgtgata      1560
ctcttgggat ggctgatgtt ggaactgtgt gtgatccgag cagaagctgc tccgtcatag      1620
aagatgatgt tttacaagct gccttcacca cagcccatga attaggccac gtgtttaaca      1680
tgccacatga tgatgcaaag cagtgtgcca gccttaatgg tgtgaaccag gattcccaca      1740
tgatggcgtc aatgctttcc aacctggacc acagccagcc ttggtctcct tgcagtgcct      1800
acatgattac atcatttctg gataatggtc atgggaatg tttgatggac aagcctcaga      1860
atcccataca gctcccaggc gatctccctg gcacctcgta cgatgccaac cggcagtgcc      1920
agtttacatt tggggaggac tccaaacact gccccgatgc agccagcaca tgtagcacct      1980
tgtggtgtac cggcacctct ggtgggtgc tggtgtgtca aaccaaacac ttcccgtggg      2040
cggatggcac cagctgtgga gaagggaat ggtgtatcaa cggcaagtgt gtgaacaaaa      2100
ccgacagaaa gcattttgat acgcctttc atggaagctg gggaatgtgg gggccttggg      2160
gagactgttc gagaacgtgc ggtggaggag tccagtacac gatgagggaa tgtgacaacc      2220
cagtcccaaa gaatggaggg aagtactgtg aaggcaaacg agtgcgctac agatcctgta      2280
```

```
accttgagga ctgtccagac aataatggaa aaacctttag agaggaacaa tgtgaagcac    2340
acaacgagtt ttcaaaagct tcctttggga gtgggcctgc ggtggaatgg attcccaagt    2400
acgctggcgt ctcaccaaag gacaggtgca agctcatctg ccaagccaaa ggcattggct    2460
acttcttcgt tttgcagccc aaggttgtag atggtactcc atgtagccca gattccacct    2520
ctgtctgtgt gcaaggacag tgtgtaaaag ctggttgtga tcgcatcata gactccaaaa    2580
agaagtttga taaatgtggt gtttgcgggg gaaatggatc tacttgtaaa aaatatcag     2640 gatcagttac tagtgcaaaa cctggatatc atgatatcat cacaattcca actggagcca    2700
ccaacatcga agtgaaacag cggaaccaga ggggatccag gaacaatggc agctttcttg    2760
ccatcaaagc tgctgatggc acatatattc ttaatggtga ctacactttg tccaccttag    2820
agcaagacat tatgtacaaa ggtgttgtct tgaggtacag cggctcctct gcggcattgg    2880
aaagaattcg cagctttagc cctctcaaag agcccttgac catccaggtt cttactgtgg    2940
gcaatgccct tcgacctaaa attaaataca cctacttcgt aaagaagaag aaggaatctt    3000
tcaatgctat ccccactttt tcagcatggg tcattgaaga gtggggcgaa tgttctaagt    3060
catgtgaatt gggttggcag agaagactgg tagaatgccg agacattaat ggacagcctg    3120
cttccgagtg tgcaaaggaa gtgaagccag ccagcaccag accttgtgca gaccatccct    3180
gcccccagtg gcagctgggg gagtggtcat catgttctaa gacctgtggg aagggttaca    3240 aaaaagaag cttgaagtgt ctgtcccatg atggagggggt gttatctcat gagagctgtg    3300 atccttaaa gaaacctaaa catttcatag acttttgcac aatggcagaa tgcagttaag    3360
tggtttaagt ggtgttagct ttgagggcaa ggcaaagtga ggaagggctg gtgcagggaa    3420
agcaagaagg ctggagggat ccagcgtatc ttgccagtaa ccagtgaggt gtatcagtaa    3480
ggtgggatta tggggtaga tagaaaagga gttgaatcat cagagtaaac tgccagttgc     3540
aaatttgata ggatagttag tgaggattat taacctctga gcagtgatat agcataataa    3600
agccccgggc attattatta ttatttcttt tgttacatct attacaagtt tagaaaaaac    3660
aaagcaattg tcaaaaaaag ttagaactat tacaaccct gtttcctggt acttatcaaa     3720
tacttagtat catgggggtt gggaaatgaa agtaggaga aaagtgagat tttactaaga     3780
cctgttttac tttacctcac taacaatggg gggagaaagg agtacaaata ggatctttga    3840
ccagcactgt ttatggctgc tatggtttca gagaatgttt atacattatt ctaccgaga    3900 attaaaactt cagattgttc aacatgagag aaaggctcag caacgtgaaa taacgcaaat    3960
ggcttcctct ttccttttt ggaccatctc agtctttatt tgtgtaattc attttgagga     4020
aaaaacaact ccatgtattt attcaagtgc attaaagtct acaatggaaa aaaagcagtg    4080
aagcattaga tgctggtaaa agctagagga gacacaatga gcttagtacc tccaacttcc    4140
tttctttcct accatgtaac cctgctttgg gaatatggat gtaaagaagt aacttgtgtc    4200
tcatgaaaat cagtacaatc acacaaggag gatgaaacgc cggaacaaaa atgaggtgtg    4260
tagaacaggg tcccacaggt ttggggacat tgagatcact tgtcttgtgg tggggaggct    4320
gctgaggggt agcaggtcca tctccagcag ctggtccaac agtcgtatcc tggtgaatgt    4380
ctgttcagct cttctgtgag aatatgattt tttccatatg tatatagtaa aatatgttac    4440
tataaattac atgtacttta taagtattgg tttgggtgtt ccttccaaga aggactatag    4500
ttagtaataa atgcctataa taacatattt atttttatac attttattct aatgaaaaaa    4560
acttttaaat tatatcgctt ttgtggaagt gcatataaaa tagagtattt atacaatata    4620
tgttactaga aataaaagaa cacttttgga aaaaaaaaaa aaaaaaaaa                4670
```

<210> SEQ ID NO 5
<211> LENGTH: 1000
<212> TYPE: DNA
<213> ORGANISM: Homo sapiens

<400> SEQUENCE: 5

| | | | | | |
|---|---|---|---|---|---|
| atttccttct | ttccccctct | gcacgcttgc | tagccccagc | gatcgctgct | ggcccccggg | 60 |
| taggaaagtg | gggttcctgg | ccgtttctgc | gacgctggcc | tagggcttgc | agctgctgtt | 120 |
| gagtgaaagc | acgcagactg | gcgggagccg | atcatttctc | gaatgaagaa | gaaaaagcgc | 180 |
| aattccctcc | ttatgctcta | gggaattgag | ccgcgtccca | gatcacccat | tccagaaatg | 240 |
| tgaaaccggg | ccctcacaaa | gtcgtctctg | gtgaagaggt | ggcgtgcggg | gtggggttg | 300 |
| gtggagggtg | aaggcataag | caaacatatt | ttaaaatcca | gatcgtagga | agtgtcacct | 360 |
| ggcccctcac | ccaggcatgc | tttctggggg | aagcgcaggg | ccaagctttc | cctagaaaag | 420 |
| ctggggcgaa | gagagagcag | gcggcggcta | aggagctcct | ggcaggctgg | gaaggtggag | 480 |
| aagtggggtg | aggtattttt | ctagaaagtg | tagccctagc | tcatctccta | gattggggaa | 540 |
| gagggaactg | agggaggagg | gaaggagacc | caggcagct | ccaggatagg | gaaatgttga | 600 |
| agaagggact | gcgttctcca | accgaaccct | ccctcctggg | aaccgcagcc | cagcgcggta | 660 |
| actgagttac | cgcaaccggg | cggtggggag | gaagggtggt | ccaggaaacc | ggcgagggag | 720 |
| aaaagcggtg | gaagggagag | tcttctccct | ggagcggccc | cagcagtaca | aagtgctggt | 780 |
| cacagcgccc | cttccgcccc | tagattgacg | agcagtggcg | tggagccagc | gcggaggctg | 840 |
| cccctcccc | ctcccgagcc | cgcagcgcgg | agcgcggttt | agcaccaacg | gagccggggg | 900 |
| cggcgtcttt | gggatggaaa | agggccaaag | gggaggagtg | gggtgggggt | ggggtttca | 960 |
| ctggtccact | ataaaaggac | cgctcggctg | cccggttctt | | | 1000 |

<210> SEQ ID NO 6
<211> LENGTH: 800
<212> TYPE: DNA
<213> ORGANISM: Homo sapiens

<400> SEQUENCE: 6

| | | | | | |
|---|---|---|---|---|---|
| gcactcgctg | gaaagcggct | ccgagccagg | ggctattgca | aagccagggt | gcgctaccgg | 60 |
| acggagaggg | gagagccctg | agcagagtga | gcaacatcgc | agccaaggcg | gaggccgaag | 120 |
| aggggcgcca | ggcaccaatc | tccgcgttgc | ctcagccccg | gaggcgcccc | agagcgcttc | 180 |
| ttgtcccagc | agagccactc | tgcctgcgcc | tgcctcag | tgtctccaac | tttgcgctgg | 240 |
| aagaaaaact | tcccgcgcgc | cggcagaact | gcagcgcctc | cttttagtga | ctccgggagc | 300 |
| ttcggctgta | gccggctctg | cgcgcccttc | caacgaataa | tagaaattgt | taattttaac | 360 |
| aatccagagc | aggccaacga | ggctttgctc | tcccgacccg | aactaaaggt | ccctcgctcc | 420 |
| gtgcgctgct | acgagcggtg | tctcctgggg | ctccaatgca | gcgagctgtg | cccgaggggt | 480 |
| tcggaaggcg | caagctgggc | agcgacatgg | ggaacgcgga | gcgggctccg | ggtctcgga | 540 |
| gctttgggcc | agtacccacg | ctgctgctgc | tcgccgcggc | gctactggcc | gtgtcggacg | 600 |
| cactcggcg | ccctccgag | gaggacgagg | agctagtggt | gccggagctg | gagcgcgccc | 660 |
| cgggacacgg | gaccacgcgc | ctccgcctgc | acgcctttga | ccagcagctg | gatctggagc | 720 |
| tgcggcccga | cagcagcttt | ttggcgcccg | gcttcacgct | ccagaacgtg | gggcgcaaat | 780 |
| ccgggtccga | gacgccgctt | | | | | 800 |

-continued

<210> SEQ ID NO 7
<211> LENGTH: 31
<212> TYPE: DNA
<213> ORGANISM: Artificial Sequence
<220> FEATURE:
<223> OTHER INFORMATION: primer

<400> SEQUENCE: 7
ttattgtaaa gttagggtgt gttattggat g                                31

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
aaaactaaaa caacacaaaa attaatacct aaca                             34

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
ttagggtgcg ttatcggac                                              19

<210> SEQ ID NO 10
<211> LENGTH: 29
<212> TYPE: DNA
<213> ORGANISM: Artificial Sequence
<220> FEATURE:
<223> OTHER INFORMATION: primer

<400> SEQUENCE: 10
taaaacaacg cgaaaattaa tacctaacg                                   29

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tcgaagtgaa acagcggaac                                             20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gccgctgtac ctcaagacaa                                             20

<210> SEQ ID NO 13
<211> LENGTH: 32
<212> TYPE: DNA
<213> ORGANISM: Artificial Sequence
<220> FEATURE:
<223> OTHER INFORMATION: primer

```
<400> SEQUENCE: 13
tgttagggga tagtgtgttt agtttagttg tg                                   32

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
catacacata acacataact cacaaaaaac atca                                 34

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
gatagcgcgt ttagtttagt cgc                                             23

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
taacgcgtaa ctcacgaaaa acatcg                                          26

<210> SEQ ID NO 17
<211> LENGTH: 35
<212> TYPE: DNA
<213> ORGANISM: Artificial Sequence
<220> FEATURE:
<223> OTHER INFORMATION: primer

<400> SEQUENCE: 17 tttgttttt tttgggagag gtaaatattg atatg                                 35

<210> SEQ ID NO 18
<211> LENGTH: 23
<212> TYPE: DNA
<213> ORGANISM: Artificial Sequence
<220> FEATURE:
<223> OTHER INFORMATION: primer

<400> SEQUENCE: 18
aaaaacctca ccaacaacca aca                                             23

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19 gtttttttc gggagaggta aatatcgata c                                     31

<210> SEQ ID NO 20
```

```
<211> LENGTH: 13
<212> TYPE: DNA
<213> ORGANISM: Artificial Sequence
<220> FEATURE:
<223> OTHER INFORMATION: primer

<400> SEQUENCE: 20
ccgacgaccg acg                                                        13

<210> SEQ ID NO 21
<211> LENGTH: 20
<212> TYPE: DNA
<213> ORGANISM: Artificial Sequence
<220> FEATURE:
<223> OTHER INFORMATION: primer]

<400> SEQUENCE: 21
acaaaagcct ggcctcatct                                                 20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
tcgccccaaa tgatatgaaa                                                 20

<210> SEQ ID NO 23
<211> LENGTH: 31
<212> TYPE: DNA
<213> ORGANISM: Artificial Sequence
<220> FEATURE:
<223> OTHER INFORMATION: primer

<400> SEQUENCE: 23
aattattttt tgagaagagy gttagagaat t                                    31

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
cccaaacrcc caaactac                                                   18

<210> SEQ ID NO 25
<211> LENGTH: 35
<212> TYPE: DNA
<213> ORGANISM: Artificial Sequence
<220> FEATURE:
<223> OTHER INFORMATION: primer

<400> SEQUENCE: 25
ttatgttttt gtgtatgtgt aggttttaag ttgtg                                35

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
```
actcccaaac taaacaaaac ccca 24

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
gtacgcgtag gttttaagtc gc 22

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ccgaactaaa cgaaaccccg 20

<210> SEQ ID NO 29
<211> LENGTH: 34
<212> TYPE: DNA
<213> ORGANISM: Artificial Sequence
<220> FEATURE:
<223> OTHER INFORMATION: primer

<400> SEQUENCE: 29
gtgtgttttt tttttgagga tttggagttg tttg 34

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
accaccaaaa aataaaaaaa caaaaaacaa acca 34

<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
gaggattcgg agtcgttc 18

<210> SEQ ID NO 32
<211> LENGTH: 30
<212> TYPE: DNA
<213> ORGANISM: Artificial Sequence
<220> FEATURE:
<223> OTHER INFORMATION: primer

<400> SEQUENCE: 32
ccgaaaaata aaaaaacgaa aaacgaaccg 30

<210> SEQ ID NO 33
<211> LENGTH: 25
<212> TYPE: DNA

```
<213> ORGANISM: Artificial Sequence
<220> FEATURE:
<223> OTHER INFORMATION: primer

<400> SEQUENCE: 33
tgggggatga ttgttgttgt agttg                                          25

<210> SEQ ID NO 34
<211> LENGTH: 26
<212> TYPE: DNA
<213> ORGANISM: Artificial Sequence
<220> FEATURE:
<223> OTHER INFORMATION: primer

<400> SEQUENCE: 34
caccaaacca cccaaaacca tataca                                         26

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
ggggacgatt gtcgttgtag tc                                             22

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
aaccgcccga aaccatatac g                                              21

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
cccacataaa acaaacaccc aaacca                                         26

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
tggtttgttg ggtaaggtgt ttg                                            23

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gttcgttggg taaggcgttc                                                20
```

```
<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
cataaaacga acacccgaac cg                                              22

<210> SEQ ID NO 41
<211> LENGTH: 34
<212> TYPE: DNA
<213> ORGANISM: Artificial Sequence
<220> FEATURE:
<223> OTHER INFORMATION: primer'

<400> SEQUENCE: 41
tagatatttt gtgggttttg tagtattggt attg                                 34

<210> SEQ ID NO 42
<211> LENGTH: 34
<212> TYPE: DNA
<213> ORGANISM: Artificial Sequence
<220> FEATURE:
<223> OTHER INFORMATION: primer

<400> SEQUENCE: 42
acaaaaaaaa aaaaaaacaa tataaataac ccca                                 34

<210> SEQ ID NO 43
<211> LENGTH: 22
<212> TYPE: DNA
<213> ORGANISM: Artificial Sequence
<220> FEATURE:
<223> OTHER INFORMATION: primer

<400> SEQUENCE: 43
cgggttttgt agtatcggta tc                                              22

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
cgaaaaaaaa aaaaaacgat ataaataacc ccg                                  33
```

COMPOSITIONS AND METHODS FOR DETECTING A NEOPLASIA

CROSS-REFERENCE TO RELATED APPLICATIONS

This application is a 35 U.S.C. § 371 U.S. national stage entry of International Application PCT/US2011/037926 (WO 2011/150075) having an International filing date of May 25, 2011 which claims the benefit of the following U.S. Provisional Application No. 61/348,010, filed May 25, 2010, the entire contents of which are incorporated herein by reference.

STATEMENT OF RIGHTS TO INVENTIONS MADE UNDER FEDERALLY SPONSORED RESEARCH

This work was supported by the following grants from the National Institutes of Health, Grant No. NIH K23CA127141 The government has certain rights in the invention.

BACKGROUND OF THE INVENTION

Pancreatic cancer is the fourth leading cause of cancer mortality with a death rate nearly equal to the incidence of this disease. Detection of cancer specific, abnormally DNA methylated gene promoter sequences has emerged as one of the leading tumor biomarker detection strategies. Recently, there have been successful reports of DNA methylation screening using various body fluids, such as stool for detection of colorectal cancer, sputum for lung cancer, and urine for prostate cancer.

However, in pancreatic cancer no screening tool is currently available for early detection. This is particularly relevant as pancreatic cancer is often found once it is already metastatic or locally advanced and the diagnosis is often delayed because patients present with nonspecific gastrointestinal symptoms. The development of a screening modality for pancreatic cancer which identifies early stage cancers amenable to surgical curative resection would then have a potential impact in reducing mortality from this currently lethal disease.

SUMMARY OF THE INVENTION

As described below, the present invention features compositions and methods for diagnosing neoplasia (e.g., pancreatic cancer, colon cancer, lung cancer) featuring BNC1 and ADAMTS1. Advantageously, the method provides for screening serum for increased promoter methylation of BNC1 and ADAMTS1 to identify early stage neoplasia or a propensity to develop a neoplasia.

In one aspect, the invention provides a method for detecting or characterizing a neoplasia in a biologic sample of a subject, the method involving detecting the methylation of a BNC1 and/or ADAMTS1 gene, where detection of methylation detects or characterizes the presence of a neoplasia in the sample. In one embodiment, the method detects an increase in methylation relative to a reference. In another embodiment, the method detects promoter methylation or methylation of exon 1.

In another aspect, the invention provides a method for detecting or characterizing lung or colon cancer in a sample derived from a subject, the method involving detecting methylation of a BNC1 and ADAMTS1 gene, where detection of methylation detects or characterizes lung or colon cancer in the subject. In one embodiment, the method involves detecting an alteration in the sequence or expression level of a Brca1, Brca2, p16, K-ras, APC, EGFR, and/or EML-ALK4 gene or polypeptide. In another embodiment, the subject is identified as having a propensity to develop a neoplasia (e.g., is identified as a smoker, having colon polyps or adenomas, or a family history of cancer).

In another aspect, the invention provides a method for detecting or characterizing pancreatic cancer in a serum or plasma sample derived from a subject, the method involving detecting the methylation of BNC1 and ADAMTS1, where detection of methylation detects or characterizes pancreatic cancer in the subject. In one embodiment, the method detects an increase in methylation relative to a reference. In another embodiment, the method further involves imaging the subject, and localizing the cancer. In another embodiment, the method further involves detecting an alteration in the sequence or expression of a Brca1, Brca2, p16, K-ras, APC, PalB2, and/or DPC4 gene or polypeptide relative to a reference. In one embodiment, the subject is identified as having a propensity to develop a pancreatic cancer (e.g., is identified as a smoker, has a Brca1 or Brca2 mutation, pancreatic cyst, chronic pancreatitis, or a family history of cancer).

In another aspect, the invention provides a method of monitoring a subject diagnosed as having a neoplasia, the method involving detecting an alteration in promoter methylation level in a BNC1 and/or ADAMTS1 gene in a subject sample relative to a reference, where an altered level indicates an altered severity of neoplasia in the subject. In one embodiment, the reference is the level of methylation present in a sample previously obtained from the subject; is a baseline level of methylation present in a sample from the subject obtained prior to therapy; or is the level of methylation present in a normal patient sample. In another embodiment, a decreased level of methylation relative to a reference indicates a reduced severity of the neoplasia, and an increased level of methylation relative to a reference indicates an increased severity of neoplasia.

In yet another aspect, the invention provides a method for selecting a treatment for a subject diagnosed as having a neoplasia, the method involving detecting methylation of a BCN1 and/or ADAMTS1 gene, where detection of methylation indicates that epigenetic therapy should be selected for treatment of said subject. In one embodiment, the epigenetic therapy is selected from the group consisting of entinostat, SAHA (suberoylanilide hydroxamic acid), depsipeptide, azocytidine, and deazocytidine.

In another aspect, the invention provides a kit for the analysis of promoter methylation, the kit involving at least one primer capable of distinguishing between methylated and unmethylated BNC1 and ADAMTS1 promoter sequences. In one embodiment, the kit further contains a pair of primers for amplifying the promoter sequence of a reference gene. In another embodiment, the kit further contains a detectable probe, where the probe is capable of binding to the promoter sequence. In yet another embodiment, the probe is detected by fluorescence, by autoradiography, by an immunoassay, by an enzymatic assay, or by a colorimetric assay.

In various embodiments of any of the above aspects or any other aspect of the invention delineated herein, the neoplasia is a cancer that is pancreatic cancer, gastrointestinal cancer, lung cancer, colon cancer, duodenal cancer, colorectal carcinoma, neuroendocrine carcinoma, cholangiocarcinomas, or ampullary tumors. In other embodiments of the above aspects, the biologic sample is a tissue or biologic fluid sample (e.g., of blood, serum, plasma, urine, pancreatic juice, pancreatic cyst fluid, or lung lavage). In various embodiments, the reference is the level of methylation present at the promoter in a control sample. In other embodiments, the control sample is derived from a healthy subject. In still other embodiments, the methylation is detected by quantitative methylation-specific PCR (QMSP). In other embodiments, the level of methylation is quantified or the frequency of methylation is quantified. In still other embodiments, the methylation levels of the BNC1 and ADAMTS1 promoters are quantified. In still other embodiments, the method results in at least 50%-100% (e.g., 50%, 60%, 70%, 80%, 90%, 100%) sensitivity. In still other embodiments, the subject is identified as having a propensity to develop a neoplasia (e.g., is a smoker, has a Brca1 or Brca2 mutation, pancreatic cyst, chronic pancreatitis, presence of colon polyps or adenomas, or a family history of cancer). In various embodiments, the method further involves detecting an alteration in the sequence or expression level of a Brca1, Brca2, p16, K-ras, APC, PalB2, DPC4, EGFR, and/or EML-ALK4 gene or polypeptide. In still other embodiments, the alteration is a sequence alteration or alteration in expression level. In still other embodiments, the subject is a human patient. In various embodiments of the above aspects, the methylation is detected or quantified by methylation on beads or quantitative methylation-specific PCR.

The invention provides compositions and methods for detecting promoter methylation of BNC1 and ADAMTS1 genes. Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "BNC1 gene" is meant a polynucleotide encoding a BNC1 polypeptide. An exemplary BNC1 gene nucleotide sequence is publically available at GeneBank No.: NM_001717. An exemplary sequence (SEQ ID NO: 1) is provided below.

```
   1 gcggcgggggg cggccatcgt gctgcgcagc ctgggcgctt ggggagccgc ccacttcgcc
  61 gggtcgcgcc ccgacggccg gagcgtggat gcggcggcgc ccgccgagcc ggggcggacg
 121 cggggcggcc cgggcccggg agacgcgccg gcagcccggg caccgcagcg gtcgcaggat
 181 ggccgaggct atcagctgta ctctgaactg tagttgccaa agtttcaaac ccgggaaaat
 241 aaaccaccgt cagtgtgacc aatgcaagca tggatgggtg gcccacgctc taagtaagct
 301 aaggatcccc cccatgtatc caacaagcca ggtggagatt gtccagtcca atgtagtgtt
 361 tgatattagc agcctcatgc tctatgggac ccaggccatc cccgttcgcc taaaaatcct
 421 actggaccgg ctcttcagtg tgttgaagca agatgaggtt ctccagatcc tccatgcctt
 481 ggactggaca cttcaggatt atatccgtgg atacgtactg caggatgcat caggaaaggt
 541 gttggatcac tggagcatca tgaccagtga ggaagaagtg gccaccttgc agcagttcct
 601 tcgttttgga gagaccaaat ctatagttga actcatggca attcaagaga aagaagagca
 661 atccatcatc ataccacctt ccacagcaaa tgtagatatc agggctttca tcgagagctg
 721 cagtcacagg agttctagcc tccccactcc tgtggacaaa ggaaacccca gcagtataca
 781 ccccttttgag aacctcataa gcaacatgac tttcatgctg cctttccagt tcttcaaccc
 841 tctgcctcct gcactgatag ggtcattgcc cgaacaatat atgttggagc agggtcatga
 901 ccaaagtcag gaccccaaac aggaagtcca tgggcccttc cctgacagca gcttcttaac
 961 ttccagttcc acaccatttc aggttgaaaa agatcagtgt ttaaactgtc cggatgctat
1021 tactaaaaaa gaagacagca cccatttaag tgactccagc tcatacaaca ttgtcactaa
1081 gtttgaaagg acacagttat cccctgaggc caaagtgaag cctgagagga atagccttgg
1141 tacaaagaag ggccgggtgt tctgcactgc atgtgagaag accttctatg acaaaggcac
1201 cctcaaaatc cactacaatg ccgtccactt gaagatcaag cataagtgca ccatcgaagg
1261 gtgtaacatg gtgttcagct ccctaaggag ccggaatcgc catagcgcca accccaaccc
1321 tcggctgcac atgccaatga acagaaataa ccgggacaaa gacctcagga acagcctgaa
```

-continued

```
1381 cctggccagc tctgagaact acaagtgccc aggtttcaca gtgacgtccc cagactgtag 1441 gcctcctccc agctaccctg gttcaggaga ggattccaaa ggccaaccag ccttcccaaa 1501 cattgggcaa aatggtgtgc tttttcccaa cctaaagaca gtccagccag tccttccttt 1561 ctaccgcagt ccagccacgc ctgccgaggt agcaaacacg cctgggatac tcccttccct 1621 cccgctgttg tcctcttcaa tcccagaaca gctcatttca aacgaaatgc catttgatgc 1681 ccttcccaag aagaaatcca ggaagtccag tatgcctatc aaaatagaga aagaagctgt 1741 ggaaatagct aatgagaaaa gacacaacct cagctcagat gaagacatgc cctacaggt 1801 ggtcagtgaa gatgagcagg aggcctgcag tcctcagtca cacagagtat ctgaggagca 1861 gcatgtacag tcaggaggct tagggaagcc tttccctgaa ggggagaggc cctgccatcg 1921 tgaatcagta attgagtcca gtggagccat cagccaaacc cctgagcagg ccacacacaa 1981 ttcagagagg gagactgagc agacaccagc attgatcatg gtgccaaggg aggtcgagga 2041 tggtggccat gaacactact tcacacctgg gatggaaccc caagttcctt tttctgacta 2101 catggaactg cagcagcgcc tgctggctgg gggactcttc agtgctttgt ccaacagggg 2161 aatggctttt ccttgtcttg aagattctaa agaactggag cacgtgggtc agcatgcatt 2221 agcaaggcag atagaagaaa atcgcttcca gtgtgacatc tgcaagaaga cctttaaaaa 2281 tgcttgtagt gtgaaaattc atcacaagaa tatgcatgtc aaagaaatgc acacatgcac 2341 agtggagggc tgtaatgcta cctttccctc ccgcaggagc agagacagac acagctcaaa 2401 cctaaacctc caccaaaaag cattgagcca ggaagcattg gagagtagtg aagatcattt 2461 ccgtgcagct taccttctga aagatgtggc taaggaagcc tatcaggatg tggcttttac 2521 acagcaagcc tcccagacat ctgtcatctt caaaggaaca agtcgaatgg gcagtctggt 2581 ttacccaata acgcaagtcc acagtgccag cctggagagc tacaactctg gcccccttgag 2641 cgagggcacc atcctggatt tgagcactac ctcgagcatg aagtcagaga gtagcagcca 2701 ttcttcctgg gactctgacg gggtgagtga ggaaggcact gtgcttatgg aggacagtga 2761 tgggaactgt gaagggtcga gccttgtccc tggggaagat gagtacccca tctgtgtcct 2821 gatggagaag gctgaccaga gccttgctag cctgccttct gggttgccca taacctgtca 2881 tctctgccaa aagacataca gtaacaaagg gacctttagg gcccactaca aaactgtgca 2941 cctccggcag ctccacaaat gcaaagtacc aggctgcaac accatgtttt cgtctgttcg 3001 cagtcgaaac agacacagcc agaatcccaa cctgcacaaa agcctggcct catctccaag 3061 tcacctccag taacaagatg gcaaaccaag tatgctcaga taagcttttt tcataattca 3121 ggaataaagt agtccataga aatgtttctg tttcatatca tttggggcga gtcaggcaaa 3181 agtatttgat ttgactttat agttttccac agcacaatga gcaaaagaca aacctcgtgg 3241 gaagatgaca ctggggcagc ccttcctatt attttttctta gcccaagagg tctttcactg 3301 atacaaggaa aacttgcaga aatgtgattt ttcccagatt tgtttacatg ttccctggga 3361 cagatccagg tctgcagatc gacaccagtg ggcccaggac ctgggggtgg ctttaaatga 3421 ggcttgcagt gttaaaggtc ttggataaga agggtcctgg ggaagaagac tctgtggaca 3481 agataccagt ccccaaaaca gcattttcag ttccttcttc aattagtttg aaatccagac 3541 ctgagtttgg aagactgatt ttttgagacc atccctgtgt ttggagtgga taattgtccc 3601 tcccctcagc cctgcaccag aggtctcata tgttacccca gggagttctc agaggattgg 3661 gttggcctct aacatgttcc ttgttaattc ttgttctgta acatgcattc aagaagctag 3721 gggaaaaata tctcatgcac ttaaataatg gtcttcaatt taatttaaaa atattttgac
```

```
3781 aatatttaat ttgtgcttat gtggtgtttg gtgtgagtgc agatattgca ctgtgtcacc 3841 tctggatctc tgctcagaag cagaacaagt gatgacctaa atgtcaaaat cactgctcgt 3901 tttcatttgg tgaacttcaa actctgttct ttttggtcac ctgtggaatg aatgcaagca 3961 tgattttggc aggaacattt gtacatattc tgccgtagat aatgtggttc tgatggttgt 4021 tgtgtatttt cagtatcact ggatccctca gtcttcaccg ttttataaac gtataagatt 4081 aggatgaact tttgaattta cttggtagga aaaaaagtag gacattattg ccatattgta 4141 tgtcttaata tttaacttat tcggaaatat attccacact gttacataca ttttccatgg 4201 tagaaaggaa gttcagtcag tcctgtggaa tgaaaccatc tcctaaaatt cagcatttgc 4261 agcattctaa aagcctgtgt aggtacaagg acattgattt tgtattcaga attcaagtta 4321 actatctttt aaattcgtgg ttgatgtaag taataaaaaa cattcttaaa gttgagggtt 4381 ataagagaga ttatttctgt ggtctaaagg ttaaaaagcc aacaacctgt taccaattat 4441 ttcagctttt tttgttttaa taagtgtgac aacttaaaac ttgtttctat ttaaagtgaa 4501 atgtatcttt caactgttta gttacccagc tgtttaatat tccagtcttc ccaaagtgaa 4561 aagatttgta tacaaatgtt ttctatgatt taataaaaat atatggcaca ccaaaaaaaa 4621 aaaaaaa
```

By "BNC1 promoter" is meant a polynucleotide sequence sufficient to direct expression of a BNC1 coding sequence. The sequence of an exemplary BNC1 promoter (BNC1 at chr15:81715659-81744472) (SEQ ID NO: 2) and the BNC1 Exon 1 (SEQ ID NO: 3) is provided below:

```
BNC1 promoter region upstream 1 kb from Exon 1
gtttccttttcaaggatccccaccagcagcaaggcaggtggaagaaactg agggaagaggaagcaggaccccgccgcccccccagtctagccttttacag actccttttaaggagctgaagaggttgggagaggcttgccctgccccggg gcagcagaaacccgggcgctgctgcagcagctgtgggcgatctccgtcag ctcctgggctccaggatcctgcggcctcagcccctccgcgtctactctcg gggccaccacctccagttggcttctccagggcacttcatttcattccgtc cctagcatccaataagacgcgaaaaacttaatcccattttacaactgaag ccactgaggcccagagagcaaagccatttgtcctgggaaagtggtcaagc tgggactttgactcttcagaccacccaagggaaggggtgtgtgtgtgtgt gtgtgtgtgtgcgtgtgcggtgggggcgcttgttttgagttcttaag aaaacctcctggcgaccccttcttccacatcccaagacgctcgtcccgc actttctcgggaatgaggtttctgcaggcgagggcggcgctgccttcttc ctccgcggcagtgagaccccgagggcgccccagggtaggaggggaggccg aatcatctcctgagaagagcgccagagaacttcagagcgtttcgcccttc cccgggagaggcaaacaccgacacgtctgtgtcttttaccaacaagtgcc ttcaagcccggcggggcagacacctccgcgccggccgccggcgaggtct ccgcggtctgcgggggccacggcctcgcctcagctgcgctgatttagggc gttatccggtcccggggcgggaggcggcctcccgggcggcgaagcagcgc ccgcggcgtggggcgaccgcgcggtgggcggaggggcaggggggaggggcg gagaggcgtccccggggcgcaggggggcgggcgtgcgggcacacgcggtgc BNC1 Exon 1
GCGGCGGGGGCGGCCATCGTGCTGCGCAGCCTGGGCGCTTGGGGAGCCGC

CCACTTCGCCGGGTCGCGCCCCGACGGCCGGAGCGTGGATGCGGCGGCGC

CCGCCGAGCCGGGGCGGACGCGGGGCGGCCCGGGCCCGGGAGACGCGCCG

GCAGCCCCGGCACCGCAGCGGTCGCAGGATGGCCGAGgtaagcgcggcgc
```

By "ADAMTS1 gene" is meant a polynucleotide sequence encoding a ADAMTS1 protein. An exemplary ADAMTS1 gene sequence is publically available at GeneBank No.: NM_006988. An exemplary ADAMTS1 gene sequence (SEQ ID NO: 4) is provided below:

```
  1 gcactcgctg gaaagcggct ccgagccagg ggctattgca aagccagggt gcgctaccgg 61 acggagaggg gagagccctg agcagagtga gcaacatcgc agccaaggcg gaggccgaag 121 aggggcgcca ggcaccaatc tccgcgttgc ctcagccccg gaggcgcccc agagcgcttc 181 ttgtcccagc agagccactc tgcctgcgcc tgcctctcag tgtctccaac tttgcgctgg 241 aagaaaaact tcccgcgcgc cggcagaact gcagcgcctc cttttagtga ctccgggagc 301 ttcggctgta gccggctctg cgcgcccttc caacgaataa tagaaattgt taattttaac 361 aatccagagc aggccaacga ggctttgctc tcccgacccg aactaaaggt ccctcgctcc
```

-continued

```
 421 gtgcgctgct acgagcggtg tctcctgggg ctccaatgca cgagctgtg cccgaggggt 481 tcggaaggcg caagctgggc agcgacatgg ggaacgcgga gcgggctccg gggtctcgga 541 gctttgggcc cgtacccacg ctgctgctgc tcgccgcggc gctactggcc gtgtcggacg 601 cactcgggcg cccctccgag gaggacgagg agctagtggt gccggagctg gagcgcgccc 661 cgggacacgg gaccacgcgc ctccgcctgc acgcctttga ccagcagctg gatctggagc 721 tgcggcccga cagcagcttt ttggcgcccg gcttcacgct ccagaacgtg gggcgcaaat 781 ccgggtccga gacgccgctt ccggaaaccg acctggcgca ctgcttctac tccggcaccg 841 tgaatggcga tcccagctcg gctgccgccc tcagcctctg cgaggcgtg cgcggcgcct 901 tctacctgct gggggaggcg tatttcatcc agccgctgcc cgccgccagc gagcgcctcg 961 ccaccgccgc cccaggggag aagccgccgg caccactaca gttccacctc ctgcggcgga 1021 atcggcaggg cgacgtcggc ggcacgtgcg gggtcgtgga cgacgagccc cggccgactg 1081 ggaaagcgga gaccgaagac gaggacgaag ggactgaggg cgaggacgaa ggggctcagt 1141 ggtcgccgca ggacccggca ctgcaaggcg taggacagcc cacaggaact ggaagcataa 1201 gaaagaagcg atttgtgtcc agtcaccgct atgtggaaac catgcttgtg cagaccagt 1261 cgatggcaga attccacggc agtggtctaa agcattacct tctcacgttg ttttcggtgg 1321 cagccagatt gtacaaacac cccagcattc gtaattcagt tagcctggtg gtggtgaaga 1381 tcttggtcat ccacgatgaa cagaagggc cggaagtgac ctccaatgct gccctcactc 1441 tgcggaactt ttgcaactgg cagaagcagc acaacccacc cagtgaccgg gatgcagagc 1501 actatgacac agcaattctt ttcaccagac aggacttgtg tgggtcccag acatgtgata 1561 ctcttgggat ggctgatgtt ggaactgtgt gtgatccgag cagaagctgc tccgtcatag 1621 aagatgatgg tttacaagct gccttcacca cagcccatga attaggccac gtgtttaaca 1681 tgccacatga tgatgcaaag cagtgtgcca gccttaatgg tgtgaaccag gattcccaca 1741 tgatggcgtc aatgctttcc aacctggacc acagccagcc ttggtctcct tgcagtgcct 1801 acatgattac atcatttctg gataatggtc atggggaatg tttgatggac aagcctcaga 1861 atcccataca gctcccaggc gatctccctg gcacctcgta cgatgccaac cggcagtgcc 1921 agtttacatt tggggaggac tccaaacact gccccgatgc agccagcaca tgtagcacct 1981 tgtggtgtac cggcacctct ggtggggtgc tggtgtgtca aaccaaacac ttcccgtggg 2041 cggatggcac cagctgtgga aagggaaat ggtgtatcaa cggcaagtgt gtgaacaaaa 2101 ccgacagaaa gcattttgat acgccttttc atggaagctg gggaatgtgg gggccttggg 2161 gagactgttc gagaacgtgc ggtggaggag tccagtacac gatgagggaa tgtgacaacc 2221 cagtcccaaa gaatggaggg aagtactgtg aaggcaaacg agtgcgctac agatcctgta 2281 accttgagga ctgtccagac aataatggaa aaacctttag agaggaacaa tgtgaagcac 2341 acaacgagtt tcaaaagct tcctttggga gtgggcctgc ggtggaatgg attcccaagt 2401 acgctggcgt ctcaccaaag gacaggtgca agctcatctg ccaagccaaa ggcattggct 2461 acttcttcgt tttgcagccc aaggttgtag atggtactcc atgtagccca gattccacct 2521 ctgtctgtgt gcaaggacag tgtgtaaaag ctggttgtga tcgcatcata gactccaaaa 2581 agaagtttga taaatgtggt gtttgcgggg gaaatggatc tacttgtaaa aaatatcag 2641 gatcagttac tagtgcaaaa cctggatatc atgatatcat cacaattcca actgagcca 2701 ccaacatcga agtgaaacag cggaaccaga ggggatccag gaacaatggc agctttcttg 2761 ccatcaaagc tgctgatggc acatatatc ttaatggtga ctacactttg tccaccttag 2821 agcaagacat tatgtacaaa ggtgttgtct tgaggtacag cggctcctct gcggcattgg
```

```
-continued
2881  aaagaattcg cagctttagc cctctcaaag agcccttgac catccaggtt cttactgtgg 2941  gcaatgccct tcgacctaaa attaaataca cctacttcgt aaagaagaag aaggaatctt 3001  tcaatgctat ccccactttt tcagcatggg tcattgaaga gtggggcgaa tgttctaagt 3061  catgtgaatt gggttggcag agaagactgg tagaatgccg agacattaat ggacagcctg 3121  cttccgagtg tgcaaaggaa gtgaagccag ccagcaccag accttgtgca gaccatccct 3181  gcccccagtg gcagctgggg gagtggtcat catgttctaa gacctgtggg aagggttaca 3241  aaaaagaag cttgaagtgt ctgtcccatg atggaggggt gttatctcat gagagctgtg 3301  atcctttaaa gaaacctaaa catttcatag acttttgcac aatggcagaa tgcagttaag 3361  tggtttaagt ggtgttagct ttgagggcaa ggcaaagtga ggaagggctg gtgcagggaa 3421  agcaagaagg ctggagggat ccagcgtatc ttgccagtaa ccagtgaggt gtatcagtaa 3481  ggtgggatta tgggggtaga tagaaaagga gttgaatcat cagagtaaac tgccagttgc 3541  aaatttgata ggatagttag tgaggattat taacctctga gcagtgatat agcataataa 3601  agccccgggc attattatta ttatttcttt tgttacatct attacaagtt tagaaaaaac 3661  aaagcaattg tcaaaaaaag ttagaactat tacaacccct gtttcctggt acttatcaaa 3721  tacttagtat catgggggtt gggaaatgaa aagtaggaga aaagtgagat tttactaaga 3781  cctgttttac tttacctcac taacaatggg gggagaaagg agtacaaata ggatctttga 3841  ccagcactgt ttatggctgc tatggtttca gagaatgttt atacattatt tctaccgaga 3901  attaaaactt cagattgttc aacatgagag aaaggctcag caacgtgaaa taacgcaaat 3961  ggcttcctct ttcctttttt ggaccatctc agtctttatt tgtgtaattc attttgagga 4021  aaaaacaact ccatgtattt attcaagtgc attaaagtct acaatggaaa aaaagcagtg 4081  aagcattaga tgctggtaaa agctagagga gacacaatga gcttagtacc tccaacttcc 4141  tttcttcct accatgtaac cctgctttgg gaatatggat gtaaagaagt aacttgtgtc 4201  tcatgaaaat cagtacaatc acacaaggag gatgaaacgc cggaacaaaa atgaggtgtg 4261  tagaacaggg tcccacaggt ttggggacat tgagatcact tgtcttgtgg tggggaggct 4321  gctgaggggt agcaggtcca tctccagcag ctggtccaac agtcgtatcc tggtgaatgt 4381  ctgttcagct cttctgtgag aatatgattt tttccatatg tatatagtaa aatatgttac 4441  tataaattac atgtacttta taagtattgg tttgggtgtt ccttccaaga aggactatag 4501  ttagtaataa atgcctataa taacatattt atttttatac atttatttct aatgaaaaaa 4561  acttttaaat tatatcgctt ttgtggaagt gcatataaaa tagagtattt atacaatata 4621  tgttactaga aataaaagaa cacttttgga aaaaaaaaaa aaaaaaaaa
```

By "ADAMTS1 promoter" is meant is meant a polynucleotide sequence sufficient to direct expression of a BNC1 coding sequence. The sequence of an exemplary AdamTS1 (ADAMTS1 at chr21:27130477-27139599) promoter (SEQ ID NO: 5) and the ADAMTS1 Exon 1 (SEQ ID NO: 6) is provided below:

```
ADAMTS1 promoter region upstream 1 kb from Exon 1
atttccttctttccccctctgcacgcttgctagcccagcgatcgctgct ggcccccgggtaggaaagtgggggttcctggccgtttctgcgacgctggcc tagggcttgcagctgctgttgagtgaaagcacgcagactggcgggagccg atcatttctcgaatgaagaagaaaaagcgcaattccctccttatgctcta gggaattgagccgcgtcccagatcacccattccagaaatgtgaaaccggg ccctcacaaagtcgtctctggtgaagaggtggcgtgcggggtggggttg gtggagggtgaaggcataagcaaacatattttaaaatccagatcgtagga agtgtcacctggcccctcacccaggcatgctttctgggggaagcgcaggg ccaagctttccctagaaaagctggggcgaagagagagcaggcggcggcta aggagctcctggcaggctgggaaggtggagaagtggggtgaggtatttt ctagaaagtgtagccctagctcatctcctagattggggaagagggaactg agggaggagggaaggagacccagggcagctccaggatagggaaatgttga agaagggactgcgttctccaaccgaaccctccctcctgggaaccgcagcc
```

-continued cagcgcggtaactgagttaccgcaaccgggcggtggggaggaagggtggt ccaggaaaccggcgagggagaaaagcggtggaagggagagtcttctccct ggagcggcccagcagtacaaagtgctggtcacagcgcccttccgcccc tagattgacgagcagtggcgtggagccagcgcggaggctgccccctcccc ctcccgagcccgcagcgcggagcgcggtttagcaccaacggagccggggg cggcgtctttgggatggaaaagggccaaggggaggagtggggtggggt gggggtttcactggtccactataaaaggaccgctcggctgccggttctt ADAMTS1 Exon 1
GCACTCGCTGGAAAGCGGCTCCGAGCCAGGGGCTATTGCAAAGCCAGGGT

GCGCTACCGGACGGAGAGGGGAGAGCCCTGAGCAGAGTGAGCAACATCGC

AGCCAAGGCGGAGGCCGAAGAGGGGCGCCAGGCACCAATCTCCGCGTTGC

CTCAGCCCCGGAGGCGCCCCAGAGCGCTTCTTGTCCCAGCAGAGCCACTC

TGCCTGCGCCTGCCTCTCAGTGTCTCCAACTTTGCGCTGGAAGAAAAACT

TCCCGCGCGCCGGCAGAACTGCAGCGCCTCCTTTTAGTGACTCCGGGAGC

TTCGGCTGTAGCCGGCTCTGCGCGCCCTTCCAACGAATAATAGAAATTGT

TAATTTTAACAATCCAGAGCAGGCCAACGAGGCTTTGCTCTCCCGACCCG

AACTAAAGGTCCCTCGCTCCGTGCGCTGCTACGAGCGGTGTCTCCTGGGG

CTCCAATGCAGCGAGCTGTGCCCGAGGGGTTCGGAAGGCGCAAGCTGGGC

AGCGACATGGGGAACGCGGAGCGGGCTCCGGGGTCTCGGAGCTTTGGGCC

AGTACCCACGCTGCTGCTGCTCGCCGCGGCGCTACTGGCCGTGTCGGACG

CACTCGGGCGCCCCTCCGAGGAGGACGAGGAGCTAGTGGTGCCGGAGCTG

GAGCGCGCCCCGGGACACGGGACCACGCGCCTCCGCCTGCACGCCTTTGA

CCAGCAGCTGGATCTGGAGCTGCGGCCCGACAGCAGCTTTTTGGCGCCCG

GCTTCACGCTCCAGAACGTGGGGCGCAAATCCGGGTCCGAGACGCCGCTT

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%. An alteration may be a change in sequence relative to a reference sequence or a change in expression level, activity, or epigenetic marker (e.g., promoter methylation or histone alterations).

By "biologic sample" is meant any tissue, cell, fluid, or other material derived from an organism.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "clinical aggressiveness" is meant the severity of the neoplasia. Aggressive neoplasias are more likely to metastasize than less aggressive neoplasias. While conservative methods of treatment are appropriate for less aggressive neoplasias, more aggressive neoplasias require more aggressive therapeutic regimens.

By "control" is meant a standard of comparison. For example, the methylation level present at a promoter in a neoplasia may be compared to the level of methylation present at that promoter in a corresponding normal tissue.

By "diagnostic" is meant any method that identifies the presence of a pathologic condition or characterizes the nature of a pathologic condition (e.g., a neoplasia). Diagnostic methods differ in their sensitivity and specificity. While a particular diagnostic method may not provide a definitive diagnosis of a condition, it suffices if the method provides a positive indication that aids in diagnosis.

By "frequency of methylation" is meant the number of times a specific promoter is methylated in a number of samples.

By "increased methylation" is meant a detectable positive change in the level, frequency, or amount of methylation. Such an increase may be by 5%, 10%, 20%, 30%, or by as much as 40%, 50%, 60%, or even by as much as 75%, 80%, 90%, or 100%. In certain embodiments, the detection of any methylation in an AdamTS1 or BNC promoter in a subject sample is sufficient to identify the subject as having a neoplasia, a pre-cancerous lesion, or the propensity to develop a neoplasia.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By "methylation level" is meant the number of methylated alleles. Methylation level can be represented as the methylation present at a target gene/reference gene×100. Any ratio that allows the skilled artisan to distinguish neoplastic tissue from normal tissue is useful in the methods of the invention. One skilled in the art appreciates that the cutoff value is selected to optimize both the sensitivity and the specificity of the assay. In certain embodiments, merely detecting promoter methylation of BNC1 and AdamTS1 genes in a biological sample of a subject is sufficient to identify the subject as having cancer, a pre-cancerous lesion, or having a propensity to develop cancer.

By "tumor marker profile" is meant an alteration present in a subject sample relative to a reference. In one embodiment, a tumor marker profile includes promoter methylation of BNC1 and/or AdamTS1 genes, as well as mutations present in Brca1, p16, K-ras, APC, PalB2, DPC4, EGFR, EML-ALK4 or other marker known in the art.

By "sensitivity" is meant the percentage of subjects with a particular disease that are correctly detected as having the disease. For example, an assay that detects 98/100 of carcinomas has 98% sensitivity.

By "severity of neoplasia" is meant the degree of pathology. The severity of a neoplasia increases, for example, as the stage or grade of the neoplasia increases.

By "specificity" is meant the percentage of subjects without a particular disease who test negative.

By "neoplasia" is meant any disease that is caused by or results in inappropriately high levels of cell division, inappropriately low levels of apoptosis, or both. For example, cancer is an example of a neoplasia. Examples of cancers include, without limitation, pancreatic cancer, including islet cell and adenocarinomas), duodenal cancers, cholangiocarcinomas, ampullary tumors, leukemia's (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colorectal carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, neuroendocrine carcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

By "periodic" is meant at regular intervals. Periodic patient monitoring includes, for example, a schedule of tests that are administered daily, bi-weekly, bi-monthly, monthly, bi-annually, or annually.

By "promoter" is meant a nucleic acid sequence sufficient to direct transcription. In general, a promoter includes, at least, 50, 75, 100, 125, 150, 175, 200, 250, 300, 400, 500, 750, 1000, 1500, or 2000 nucleotides upstream of a given coding sequence (e.g., upstream of the coding sequence for BNC1 and ADAMTS1 polypeptides).

By "marker" is meant any protein or polynucleotide having an alteration in methylation, expression level or activity that is associated with a disease or disorder.

By "reduces" is meant a negative alteration of at least 10%, 25%, 50%, 75%, or 100%.

By "reference" is meant a standard or control condition. Exemplary references include a baseline of methylation present in a healthy control subject or a standardized curve.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

BRIEF DESCRIPTION OF THE DRAWINGS

FIG. 1A depicts a schematic that is a step-wise representation of the screening method used to identify epigenetic biomarkers. FIG. 1B depicts the results of methylation analysis of 8 cancer-specific genes in pancreatic cancer cell lines. M=methylation signal; U=unmethylated signal. IVD=in vitro methylated DNA. ddH$_2$O=water control adding no DNA. FIG. 1C is a bar graph that displays the methylation frequencies of the 8 genes in a series of pancreatic cancer patients from JHU (stage 1-4; n=143), along with a series of normal pancreas from non cancerous patients (n=4), and a series of pancreatic intraductal neoplasia (PanIN) (n=20 ranging from PanIN 1-3).

FIG. 2A shows silencing of BNC1 and ADAMTS1 genes in pancreatic cancer cell lines by a methylation specific PCR (MSP) analysis of BNC1 and ADAMTS1 gene promoter regions (upper panel depicting gel bands), and the correlation of promoter methylation with gene expression by quantitative RT-PCR) in pancreatic cancer cell lines (lower panel showing data in bar graph format. M=methylation signal; U=unmethylated signal. IVD=in vitro methylated DNA. Real-time RT-PCR expression is shown as fold change±SE relative to mock-treated cells during 5 uM 5-Aza-deoxycitidine (DAC) and 300 nM Trichostatin A (TSA) treatments. FIG. 2B shows the results of bisulfite sequencing analysis of CpG islands in the BNC1 gene promoter region. The BNC1 promoter regions is depicted as a line, with CpG regions designated as vertical slashes. TIS indicates the transcriptional start site. Location of CpG sites (bisulfite priners (BST): upstream region from −331 to +36 relative to transcriptional start site). Bisulfite sequencing analysis of the BNC1 gene in Panc1 (pancreatic cancer cell line), normal pancreas tissue, pancreatic primary tumors and HCT116 (DNMT1/3b−/−) as a negative control. Open and filled circles represent unmethylated and methylated CpG sites, respectively, and each row represents a single clone. FIG. 2C shows step-wise illustration of the nanoas say used to detect methylation in serum. DNA extraction and bisulfite conversion are carried out using methylation-on-beads (MOB). DNA is eluted using PCR buffer, and amplified using MSP modified primers and fluorophore-labeled NTPs. Samples are analyzed using MS-qFRET or gel electrophoresis.

FIG. 3 shows a statistically increased frequency of methylation when normal pancreas tissue is compared to invasive cancers. FIG. 3 also shows that BNC1 methylation could be detected at the earliest stages of pancreatic carcinogenesis (e.g. PanIN's) as compared to ADAMTS1 methylation. Normal pancreas (n=4 normal tissues, n=10 surrounding normal tissues) and Pancreatitis samples (n=30), PanIN (n=20), and tumor (stage 2; n=12), respectively. Real-time MSP is shown as fold change for Methylated signal relative to Unmethylated signal. In MSP analysis, signals for unmethylated (U) and methylated (M) DNA are shown for each sample. Horizontal bar indicates mean.

FIGS. 4A, 4B, and 4C show colony formation assays, Panc1 charts and bar graphs, and MIA-PaCa2 charts and bar graphs, respectively. FIG. 4A shows colony formation by Panc1 and MIA-PaCa2 cells transfected with pcDNA3.1 or BNC1-pcDNA3.1 and grown for 2 weeks in medium containing G418. Results are plotted as the mean colony numbers relative to pcDNA3.1 transfectants in three independent experiments (Panc1; *p=0.0275, MIA-PaCa2; *p=0.0294). FIG. 4B shows graphs that summarize cell proliferation assay in Panc1 cells, while FIG. 4C shows analogous data for MIA-PaCa cells. FIGS. 4A and 4B are each divided into a right panel, a middle panel, and a left panel, which depict relevant data for Panc1 and MIA-PaCa cells, respectively. Right panel: BNC1 transfected Panc1 cells (BNC1-pcDNA3.1) were compared with control cells transfected with empty vector (pcDNA3.1). Results are plotted as the mean cells number in three different independent experiments (Panc1; *p=0.0469; 72 hrs, **p=0.0086; 96 hrs: MIA-PaCa2, *p=0.0469; 48 hrs, *p=0.0318; 72 hrs, *p=0.0389; 96 hrs). Middle panel: Cell proliferation measured by 3H-thymidine incorporation (Panc1; *p=0.0286, MIA-PaCa2; *p=0.0256). Left panel: Invasion of Panc1 and MIA-PaCa2 cells through matrigel-coated transwells relative to control cells transfected with empty vector in three independent experiments (NS: not statistically significant).

DETAILED DESCRIPTION OF THE INVENTION

Figure 1A:
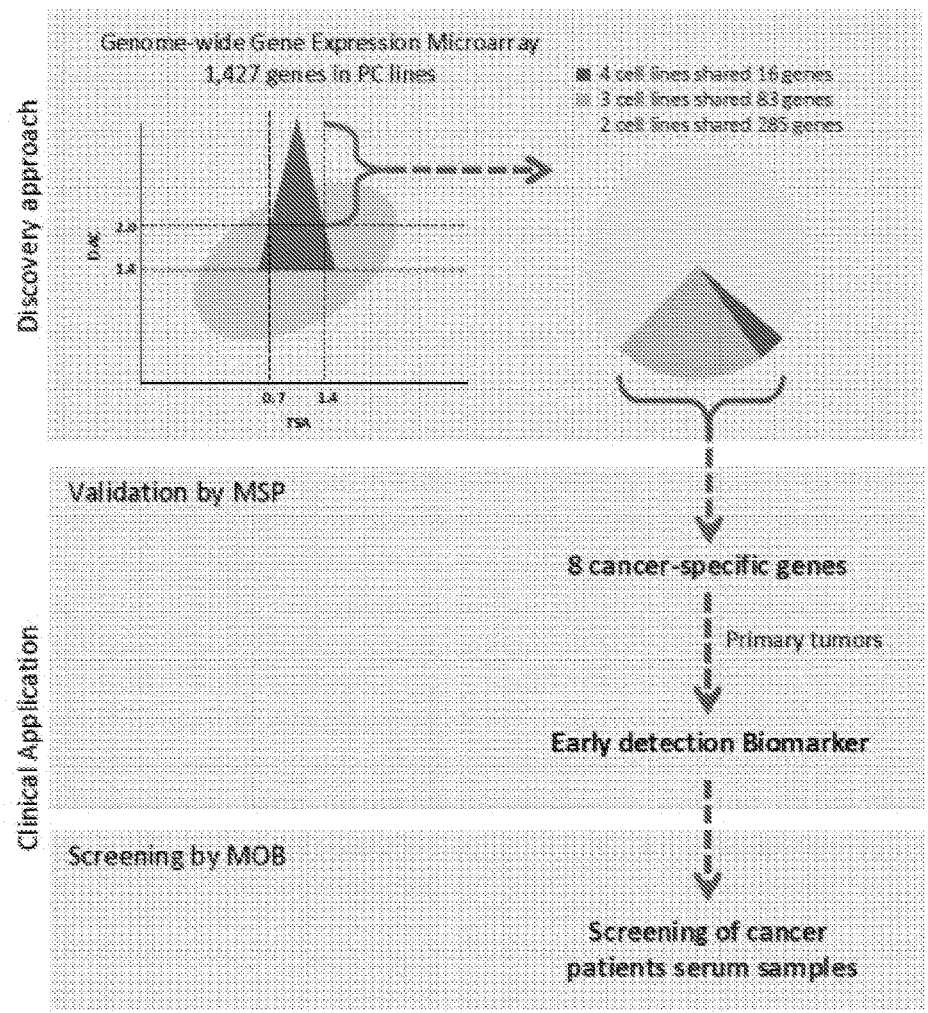
FIGS. 1A, 1B, and 1C show a schematic diagram, a gel, and a bar graph, respectively.

The invention features compositions and methods that are useful for identifying a subject as having or having a propensity to develop neoplasia (e.g., pancreatic cancer, colon cancer, lung cancer).

The invention is based, at least in part, on the discovery that detection of BNC1 and ADAMTS1 promoter methylation was useful for identifying with high sensitivity the earliest stages of pancreas cancers. Notably, detection of BNC1 and ADAMTS1 promoter methylation in circulating DNA in serum was useful for the early detection of lung, colon and pancreatic cancer, especially in high risk individuals. Moreover, BNC1 is a tumor suppressor gene in pancreatic cancer that is inactivated by promoter methylation.

A genome-wide transcriptome approach was used to identify new cancer specific DNA methylation alterations in pancreatic carcinoma. Methylation frequencies were analyzed for genes, BNC1 and ADAMTS1, by methylation specific PCR and quantitative methylation specific PCR, as well as expression analysis by real-time PCR and immunohistochemistry. A novel nanoparticle-enabled Methylation On Beads technology was used to detect very early stage pancreatic cancers. The biological role of BNC1 gene was examined by colony formation, cell proliferation, and invasion assays in pancreatic cancer cell lines. This analysis led to the identification of BNC1 (91.8%) and ADAMTS1 (66.7%) as genes that showed a high frequency of methylation in pancreas cancer tissues (n=143). BNC1 was frequently methylated in the earliest stages of pancreas carcinogenesis including carcinoma in situ or pancreatic intraepithelial neoplasia PanIN3 (100%) and Stage 1 invasive cancers (97.4%). Using the ultrasensitive nanoparticle-enabled MOB assay, these alterations were detected in serum samples from patients with pancreas cancer, with a sensitivity for BNC1 of 79% (95% CI: 0.6-0.8) and for ADAMTS1 of 48% (95% CI: 0.3-0.6) (n=42 cancers, Stages 1-4), while specificity was 88% for BNC1 (95% CI: 0.6-0.9) and 92% for ADAMTS1 (95% CI: 0.7-0.9) among 26 individuals without cancer. BNC1 overexpresstion in pancreatic cancer cell lines showed suppressive effect by colony formation, and cell proliferation, but not invasion.

Pancreatic Cancer

Pancreatic cancer is a deadly cancer with an overall 5-year survival rate of less than 5% and no improvements in survival over the last 3 decades. Pancreatic cancer currently ranks as the fourth leading cause of cancer related death in United States with an estimated 42,470 new cases and 35,240 deaths in 2009 and its incidence is rising. One of the major factors attributed to the dismal prognosis of pancreas cancer is the delayed diagnosis of the disease. Only about 10% of cases are amenable to potential curative surgical resection. However, long term 5-year survival is attainable in selected patients with early-stage pancreatic cancer who can undergo curative surgical resection. Early detection of pancreatic cancer is, therefore, thought to be the best modality for improving survival in this lethal disease. However, no screening test is available for detection of pancreatic cancer.

Pancreatic cancer is characterized by multiple genetic and epigenetic changes. In recent years, it has become apparent that pancreatic cancer is as much a disease of mis-regulated epigenetics, as it is a disease of genetic mutation. In particular, changes in DNA promoter methylation patterns likely play a crucial role in tumorigenesis and cancer progression. In order to address the need for both clinical diagnostics as well as therapeutics, many studies have employed DNA methylation of specific genes for application in diagnostics of multiple cancers. Such diagnostic tests can in principle be used for early detection of cancers, for assessing prognosis, and for therapeutics as predictors of response to therapy. Early detection of disease results in an improved clinical outcome for most types of cancer (Jemal A et al. (2011) Cancer Statistics, 2010. CA Cancer J. Clin. March-April; 61(2):133-4). Therefore, much effort has been invested in developing efficient screening technologies for early detection strategies.

Cancer Screening

Ideally, methods for cancer screening should be easy to perform, cost-effective, noninvasive, and provide a benefit to patients. Current methods of screening for pancreatic cancer are inadequate. For example, endoscopic ultrasound has shown promise for identifying high risk patients, but requires access to specialized centers and is an expensive and invasive modality that needs to be repeated at frequent intervals. The present invention provides significant advantages over existing screening technologies for pancreatic and other cancers. Significantly, the invention provides methods for detecting BNC1 and ADAMTS1 methylation. Increased methylation in BNC1 and ADAMTS1 is associated with all stages of pancreatic cancer. BNC1 gene was methylated at 100% frequency in PanIN3, which is felt to be the penultimate step prior to development of invasive carcinoma.

Interestingly, BNC1 showed a potential tumor suppressive role as measured by suppression of colony formation, cell proliferation, and invasion in pancreatic cancer cells. Methylation of BNC1 and ADAMTS1 showed high sensitivity and specificity for detecting pancreatic cancer in sera using nano-enabled methylation based technology termed Methylation-on-Beads (MOB). The results reported herein below indicate that methylation-based screening is useful for identifying subjects at risk of not only pancreatic cancer, but also, lung and colon cancers using a non-invasive inexpensive modality.

While the methods of the invention are suitable for screening the population at large, it is particularly useful for screening subjects identified as at increased risk for having a neoplasia. Subjects identified as having an increased risk of neoplasia (e.g., pancreatic cancer, lung cancer, colon cancer) include but are not limited to smokers and subjects having a Brca1 or Brca2 mutation. Subjects identified as having an increased risk of pancreatic cancer include subjects identified as having pancreatic cysts or pancreatitis, as well as patients that have a family history of pancreatic cancer, particularly in 1 or 2 relatives.

Types of Biological Samples

The level of promoter methylation in each of the genes identified herein (e.g., BNC1 and ADAMTS1) can be measured in different types of biologic samples. In one embodiment, the biologic sample is a blood, plasma, or serum sample. In another embodiment, the sample is a tissue sample that includes cells of a tissue or organ (e.g., pancreatic cells, cells of a pancreatic cyst or pancreas lesion, lung cells, and colon cells). Pancreatic tissue is obtained, for example, from a biopsy of the pancreas. In another embodiment, the biologic sample is a biologic fluid sample (e.g., blood, blood serum, plasma, urine, stool, pancreatic cyst fluid, fluid from the major/minor pancreatic duct (i.e., "pancreatic juice") lung lavage, stool, sputum, or any other biological fluid useful in the methods of the invention).

Methylation-On-Beads

In brief, Methylation-on-Beads is a single-tube method for polynucleotide extraction and bisulfite conversion that provides a rapid and highly efficient method for DNA extraction, bisulfite treatment and detection of DNA methylation using silica superparamagnetic particles (SSP). All steps are implemented without centrifugation or air drying that provides superior yields relative to conventional methods for DNA extraction and bisulfite conversion. SSP serve as solid substrate for DNA binding throughout the multiple stages of each process. Specifically, SSP are first used to capture genomic DNA from raw biological samples, processed biological samples or cultured cells. Sodium bisulfite treatment is then carried out in the presence of SSP without tube transfers. Finally, the bisulfite treated DNA is analyzed to determine the methylation status. DNA extraction yield was found to be 5-20 times the yield from conventional extraction. 90% of the input DNA was recovered after bisulfite treatment. In addition, Methylation-on-Beads total process time was completed in less than 6 hours when compared to 3 days for conventional methods. Hence, Methylation-on-Beads allows for convenient, efficient and contamination-resistant methylation detection in a single tube or other reaction platform. Methods for carrying out methylation-on-beads are known in the art, and described, for example, in PCT/US2009/000039, which is incorporated herein in its entirety.

Methylation-Specific Quantum Dot FRET

If desired, methods of the invention may be advantageously combined with methylation-specific quantum dot fluorescence resonance energy transfer (MS-qFRET). See, for example, PCT/US2009/000039, which is incorporated herein in its entirety. MS-qFRET provides for the qualitative and quantitative detection of methylated DNA, as well as for the detection of low-abundance methylated DNA. In this technique, quantum dots are used to capture methylation-specific PCR (MSP) amplicons and to determine the methylation status via fluorescence resonance energy transfer (FRET). Desirably, MS-qFRET has low intrinsic background noise, high resolution and high sensitivity. MS-qFRET detects as little as 15 pg of methylated DNA in the presence of a 10.000-fold excess of unmethylated alleles, enables reduced use of PCR (8 cycles), and allows for multiplexed analyses.

More specifically, bisulfite-treated DNA is amplified through PCR, wherein the forward primer is biotinylated and the reverse primer is labeled with an organic fluorophore. Next, streptavidin-conjugated quantum dots (QDs) are introduced to capture the labeled PCR products via streptavidin-biotin binding, bringing the QDs (serving as donors) and fluorophores (serving as acceptors) in close proximity allowing FRET to occur. Finally, PCR products are detected by emissions of fluorophores accompanied by quenching of QDs. Spectral information is processed to determine the level of DNA methylation. Fluorescence responses are measured using a fluorospectrometer.

PCR with labeled primers is run. Products are then subject to PCR purification (Qiagen Corporation) in order to recover PCR product that is free of primers, primer-dimers, Taq and dNTPs. For conjugating with quantum dots (Invitrogen Corporation), 1 µL of 100 mM NaCl is mixed with 7 µL PCR mix. 1 µL of deionized (DI) $H_2O$ is added to this mix. Finally, 1 µL of 1 nM QD is added and the mixture is left undisturbed for 15 minutes.

Mixtures of defined methylation levels ranging from 100%, 75%, 50%, 25%, and 1% of the total 150 ng input DNA are obtained. To quantify the level of methylation, a "q-score": a score that is based on the normalized FRET efficiencies of acceptor and donor emission in MS-qFRET is defined. In any FRET process, as the level of the acceptor emission increases, the decay of donor emission increases as well. The FRET efficiency can then be calculated based on the proximity ratio formalism, $$E = \frac{I_A}{I_A + I_D}$$

($I_D$ and $I_A$ corresponding to donor and acceptor intensity). Further, the q-score was determined by normalizing the calculated E for the DNA mixture to an appropriate concentration of IVD only as a methylated control (q-score=1) and NL only and as an unmethylated control (q-score=0). By including positive and negative controls in every assay a standard curve is created in order to quantify and compare methylation levels of unknown samples using low-amplification cycles.

Diagnostic Assays

The present invention provides a number of diagnostic assays that are useful for the identification or characterization of a neoplasia (e.g., pancreatic cancer, lung cancer, colon cancer). In one embodiment, a neoplasia is characterized by quantifying or determining the methylation level of one or more of the following promoters: BNC1 and ADAMTS1 in the neoplasia. In one embodiment, methylation levels are determined using quantitative methylation specific PCR (QMSP) to detect CpG methylation in genomic DNA. QMSP uses sodium bisulfate to convert unmethylated cytosine to uracil. A comparison of sodium bisulfate treated and untreated DNA provides for the detection of methylated cytosines.

While the examples provided below describe methods of detecting methylation levels using QMSP, the skilled artisan appreciates that the invention is not limited to such methods. Methylation levels are quantifiable by any standard method, such methods include, but are not limited to real-time PCR, Southern blot, bisulfite genomic DNA sequencing, restriction enzyme-PCR, MSP (methylation-specific PCR), methylation-sensitive single nucleotide primer extension (MS-SNuPE) (see, for example, Kuppuswamy et al., *Proc. Natl Acad. Sci. USA,* 88, 1143-1147, 1991), DNA microarray based on fluorescence or isotope labeling (see, for example, Adorjan Nucleic Acids Res., 30: e21 and Hou Clin. Biochem., 36:197-202, 2003), mass spectroscopy, methyl accepting capacity assays, and methylation specific antibody binding. See also U.S. Pat. Nos. 5,786,146, 6,017,704, 6,300,756, and 6,265,171.

The primers used in the invention for amplification of the CpG-containing nucleic acid in the specimen, after bisulfite modification, specifically distinguish between untreated or unmodified DNA, methylated, and non-methylated DNA. Methylation specific primers for the non-methylated DNA preferably have a T in the 3' CG pair to distinguish it from the C retained in methylated DNA, and the compliment is designed for the antisense primer. Methylation specific primers usually contain relatively few Cs or Gs in the sequence since the Cs will be absent in the sense primer and the Gs absent in the antisense primer (C becomes modified to U(uracil) which is amplified as T(thymidine) in the amplification product).

The primers of the invention embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. The primer must be sufficiently long to prime the synthesis of extension products in the presence of the inducing agent for polymerization. The exact length of primer will depend on many factors, including temperature, buffer, and nucleotide composition. The oligonucleotide primer typically contains between 12 and 27 or more nucleotides, although it may contain fewer nucleotides. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. While exemplary primers are provided herein, it is understood that any primer that hybridizes with the target sequences of the invention are useful in the method of the invention for detecting methylated nucleic acid.

In one embodiment, methylation specific primers amplify a desired genomic target using the polymerase chain reaction (PCR). The amplified product is then detected using standard methods known in the art. In one embodiment, a PCR product (i.e., amplicon) or real-time PCR product is detected by probe binding. In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Molecular Beacons (see, for example, Tyagi et al., Nature Biotechnology 14(3):303-8, 1996), Scorpions® (Molecular Probes Inc., Eugene, Oreg., USA)). In another example, a PCR product is detected by the binding of a fluorogenic dye that emits a fluorescent signal upon binding (e.g., SYBR® Green (Molecular Probes)). Such detection methods are useful for the detection of a methylation specific PCR product.

The methylation level of BNC1 and/or ADAMTS1 promoters described herein defines the methylation profile of a neoplasia. The level of methylation present at any particular promoter is compared to a reference. In one embodiment, the reference is the level of methylation present in a control sample obtained from a patient that does not have a neoplasia. In another embodiment, the reference is a baseline level of methylation present in a biologic sample derived from a patient prior to, during, or after treatment for a neoplasia. In yet another embodiment, the reference is a standardized curve.

The methylation level of any one or more of the promoters described herein (e.g., BNC1 and ADAMTS1) is used, alone or in combination with other standard methods, to characterize the neoplasia. For example, methods for detecting BNC1 or ADAMTS1 promoter methylation may be carried out prior to or concurrently with testing for alterations in other biomarkers, such as BRCA1, p16, K-ras, APC, PalB2, DPC4, EGFR, EML-ALK4 gene or polypeptide. In one embodiment, the alteration in a Brca1, p16, K-ras, APC, PalB2, DPC4, EGFR, EML-ALK4 gene is a mutation in the sequence of the gene relative to a reference. In other embodiments, the alteration is in the level of expression or activity of the Brca1, p16, K-ras, APC, PalB2, DPC4, EGFR, or EML-ALK4 gene or polypeptide. Once a subject is identified as having increased BNC1 or ADAMTS1 promoter methylation, further diagnostic testing may be carried out to localize the pathology to a particular organ or organ system. Typically, after the subject has been identified as having increased promoter methylation in BNC1 and ADAMTS1, imaging studies are carried out. Such studies include, but are not limited to, endoscopic ultrasound, MRI, CT scan, and PET scan.

If desired, diagnostic methods of the invention can be combined with conventional diagnostic methods used to determine the stage or grade of a neoplasia. Grading is used to describe how abnormal or aggressive the neoplastic cells appear, while staging is used to describe the extent of the neoplasia. The grade and stage of the neoplasia is indicative of the patient's long-term prognosis (i.e., probable response to treatment and survival). Thus, the methods of the invention are useful for predicting a patient's prognosis, and for selecting a course of treatment.

In conventional diagnostic methods, a pathologist will view a tissue sample from the tumor and determine the grade based on the degree of pathology observed. Typically, pancreatic tumors are graded from 1-4. For a grade I tumor, cells present in the sample are most similar to normal pancreatic cells. Grade 4 samples contain cells that are most dissimilar to normal pancreatic cells. High-grade neoplasias are the most deadly because they are most aggressive and fast growing. High-grade neoplasias typically move rapidly into surrounding tissues, such as lymph nodes and bones.

Stage refers to the extent of a cancer. In pancreatic cancer, for example, one staging method divides the cancer into four categories, stage I pancreatic cancer is found only in the pancreas itself or has started to spread to the tissues next to the pancreas (such as the small intestine, the stomach, or the bile duct). Stage II pancreatic cancer has spread to nearby organs such as the stomach, spleen, or colon, but has not entered the lymph nodes. Stage III pancreatic cancer has spread to the lymph nodes near the pancreas. Cancer may have spread to nearby organs. Stage 1V pancreatic cancer has spread to organs near the pancreas (stage IVA) or to organs far away from the pancreas (stage IVB). Stage IVA pancreatic cancer has spread to organs that are near the pancreas (such as the stomach, spleen, or colon) but has not spread to distant organs (such as the liver or lungs). Stage IVB pancreatic cancer has spread to distant organs (such as the liver or lungs).

Selection of a Treatment Method

Identifying the presence of increased promoter methylation in BNC1 and ADAMTS1, indicates that the subject likely has an invasive cancer or a pre-cancerous lesion (e.g., cancer-in-situ). Further diagnostic testing may be carried out to localize the pathology to a particular organ or organ system. For example, endoscopic ultrasound, MRI, CT scan, PET scan, bronchoscopy, colonoscopy, esophagogastroduodenoscopy, laparoscopic surgery to localize a lesion or any other modality known in the art may be used to characterize the neoplasia or pre-cancerous lesion (e.g. PanIN's, or precursor lung conditions such as dysplasia, carcinoma in situ, atypical adenomatous hyperplasia or precursor colonic lesions such as adenomas). Pre-cancerous lesions are likely to be susceptible to conservative treatment methods. Conservative treatment methods include, for example, cancer surveillance, which involves periodic patient monitoring using diagnostic assays of the invention, alone or in combination, with diagnostic imaging or chemoprevention.

More aggressive neoplasias are less susceptible to conservative treatment methods. For aggressive neoplasias, an aggressive method of treatment should be selected. Aggressive therapeutic regimens typically include one or more of the following therapies: surgical resection, radiation therapy, and chemotherapy. After a subject is diagnosed as having a neoplasia (e.g., prostate cancer, lung cancer, colon cancer) a method of treatment is selected. Where the methods of the invention identify a subject as having a neoplasia associated with increased promoter methylation in BNC1 and ADAMTS1, therapy to reduce this promoter methylation may be selected. For example, epigenetic therapy may be selected to relieve promoter methylation in BNC1 and ADAMTS1. Such epigenetic therapy may involve the use of histone deacetylase inhibitors or methylation inhibitors. Exemplary agents include, but are not limited to, entinostat, SAHA (suberoylanilide hydroxamic acid), depsipeptide (Fujisawa Pharmaceuticals), azocytidine, deazocytidine, romidepsin (Istodax), Vorinostat, polyamine analogues, zebularine and other novel emerging drugs targeting methylation, histone changes or the entire polycomb complex. Epigenetic therapy may be combined with more conventional therapies.

Patient Monitoring

The diagnostic methods of the invention are also useful for monitoring the course of a pre-cancerous lesion in a patient or for assessing the efficacy of a therapeutic regimen. In one embodiment, the diagnostic methods of the invention are used periodically to monitor the methylation levels of BNC1 and/or ADAMTS1. In one example, the neoplasia is characterized using a diagnostic assay of the invention prior to administering therapy. This assay provides a baseline that describes the methylation level of one or more promoters or the methylation profile of the neoplasia prior to treatment. Additional diagnostic assays are administered during the course of therapy to monitor the efficacy of a selected therapeutic regimen. A therapy is identified as efficacious when a diagnostic assay of the invention detects a decrease in methylation levels at one or more promoters relative to the baseline level of methylation.

Kits

The invention also provides kits for the diagnosis or monitoring of a neoplasia in a biological sample obtained from a subject. In various embodiments, the kit includes at least one primer or probe whose binding distinguishes between a methylated and an unmethylated BNC1 and ADAMTS1 promoter sequence, together with instructions for using the primer or probe to identify a neoplasia. In another embodiment, the kit further comprises a pair of primers suitable for use in a polymerase chain reaction (PCR). In yet another embodiment, the kit further comprises a detectable probe. In yet another embodiment, the kit further comprises a pair of primers capable of binding to and amplifying a reference sequence. In yet other embodiments, the kit comprises a sterile container which contains the primer or probe; such containers can be boxes, ampoules, bottles, vials, tubes, bags, pouches, blister-packs, or other suitable container form known in the art. Such containers can be made of plastic, glass, laminated paper, metal foil, or other materials suitable for holding nucleic acids. The instructions will generally include information about the use of the primers or probes described herein and their use in diagnosing a neoplasia. Preferably, the kit further comprises any one or more of the reagents described in the diagnostic assays described herein. In other embodiments, the instructions include at least one of the following: description of the primer or probe; methods for using the enclosed materials for the diagnosis of a neoplasia; precautions; warnings; indications; clinical or research studies; and/or references. The instructions may be printed directly on the container (when present), or as a label applied to the container, or as a separate sheet, pamphlet, card, or folder supplied in or with the container.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples that are now described; rather, the invention should be construed to include any and all applications provided herein and all equivalent variations within the skill of the ordinary artisan.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Identification of Cancer-Specific Promoter Methylation Candidate Genes in Pancreas Hypermethylome In order to identify new DNA methylation biomarkers for pancreatic cancer, previously established whole human transcriptome microarray screening was used to identify genes silenced by promoter hypermethylation. To identify global hypermethylation-dependent gene expression changes in pancreatic cancer, a genome-wide expression array-based approach was performed in four different human pancreatic cancer cell lines (PL45, MIA-PaCa2, Panc1, and Capan1) with a pharmacologic strategy using 5-aza-deoxycycytidine and Trichostatin A (TSA) using standard array-based methodology (e.g. Agilent Technologies 44K). As seen in FIG. 1A, a total of 1,427 unique genes were initially identified in four cell lines, which met the criteria for candidate hypermethylated genes in the pancreatic cancer cell lines.

In order to identify genes that only showed cancer specific methylation, the following experimental validation criteria was used: 1) the gene was expressed in normal pancreas tissue, 2) the gene displayed no/low methylation in normal pancreatic tissues (cancer-free tissues), and 3) the gene was frequently methylated in pancreas cancer cell lines, and methylation was also seen in primary tumors. Based on these criteria, 8 genes (TFPI2, ASCL2, BNC1, TWIST1, BNIP3, ADAMTS1, PNMT, and EVL) were identified that displayed cancer-specific methylation in pancreatic cancers.

Example 2: BNC1 and ADAMTS1—DNA Methylation Biomarkers for Early Detection of Pancreatic Cancer Next, the methylation status of these 8 genes (TFPI2, ASCL2, BNC1, TWIST1, BNIP3, ADAMTS1, PNMT, and EVL) was examined in a large series of primary pancreatic tumor samples (n=143; Stages 1-4) using methylation specific PCR (see Table 1).

TABLE 1

Clinical information of pancreas cancer patient primary tumor samples in this study

| | | Pancreas Primary tumors | | | | |
|---|---|---|---|---|---|---|
| | Normal (n = 4) | PanINs (N = 20) | Stage 1 (N = 38) | Stage 2 (N = 78) | Stage 3 (N = 5) | Stage 4 (N = 2) |
| Median Survival (months) | | Not Met | 43.0 | 18.0 | 14.1 | 19.6 |
| Gender | | | | | | |
| Male | 3(75%) | 9 (45%) | 9 (23.7%) | 44 (57%) | 1 (20%) | 2 (100%) |
| Femal | 1925%) | 11 (55%) | 29 (76.3%) | 34 (43%) | 4 (80%) | 0.0% |
| Grade | | | | | | |
| Well- | | 9 (45%) | 3 (7.9%) | 4 (5.1%) | 1 (20%) | 0 (0%) |
| Moderately | | 8 (40%) | 23 (60.5%) | 41 (52%) | 4 (40%) | 1 (50%) |
| Poorly | | 3 (15%) | 12 (31.6%) | 33 (42.9%) | 4 (40%) | 1 (50%) |

Figures 1B, 1C:
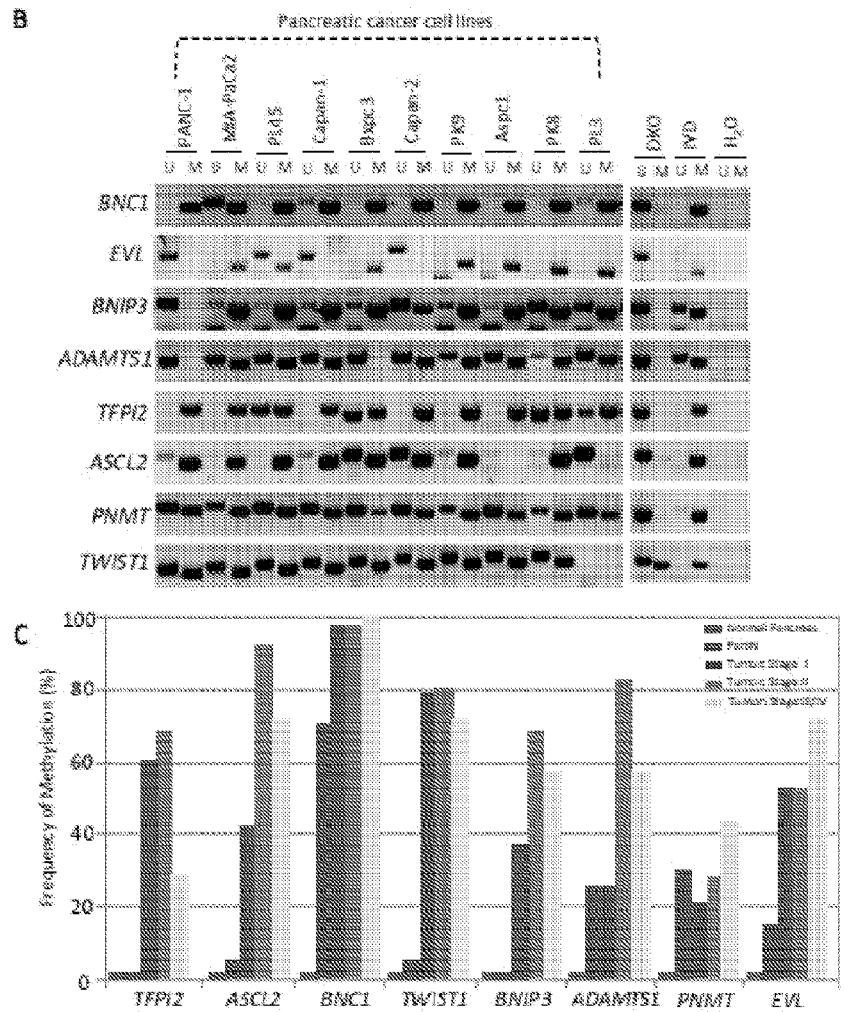

As shown in FIG. 1B, the most frequently methylated gene was BNC1 (90.5%), followed by ADAMTS1 (66.7%), TWIST1 (66.7%), ASCL2 (53.79%), BNIP3 (49%), TFPI2 (53.7%,) EVL (46.3%), and PNMT (26.5%). Interestingly, two of the genes that demonstrated frequent methylation in this cohort of primary pancreatic cancer samples, BNC1 (90.5%) and ADAMTS1 (66.7%), also showed frequent methylation in the precursor lesions of pancreatic cancer, pancreatic intraepithelial neoplasia (PanIN) lesion. Specifically, BNC1 methylation frequency was 70% (n=14/20) and ADAMTS1 methylation frequency was 25% (n=5/20).

The ability to identify high grade precursor lesions such as PanIN3 (or pancreatic carcinoma in situ) represents one of the best means for achieving early detection of pancreatic cancer, and facilitating the implementation of chemoprevention strategies (see FIG. 1C). BNC1 was methylated in PanIN 1 (56%), PanIN 2 (75%), and PanIN 3 (100%) during PanIN progression. This data indicated that DNA methylation of BNC1 gene is an early event in pancreatic carcinogenesis and that the prevalence of methylation increases with pancreatic cancer progression.

Figures 2A, 2B:
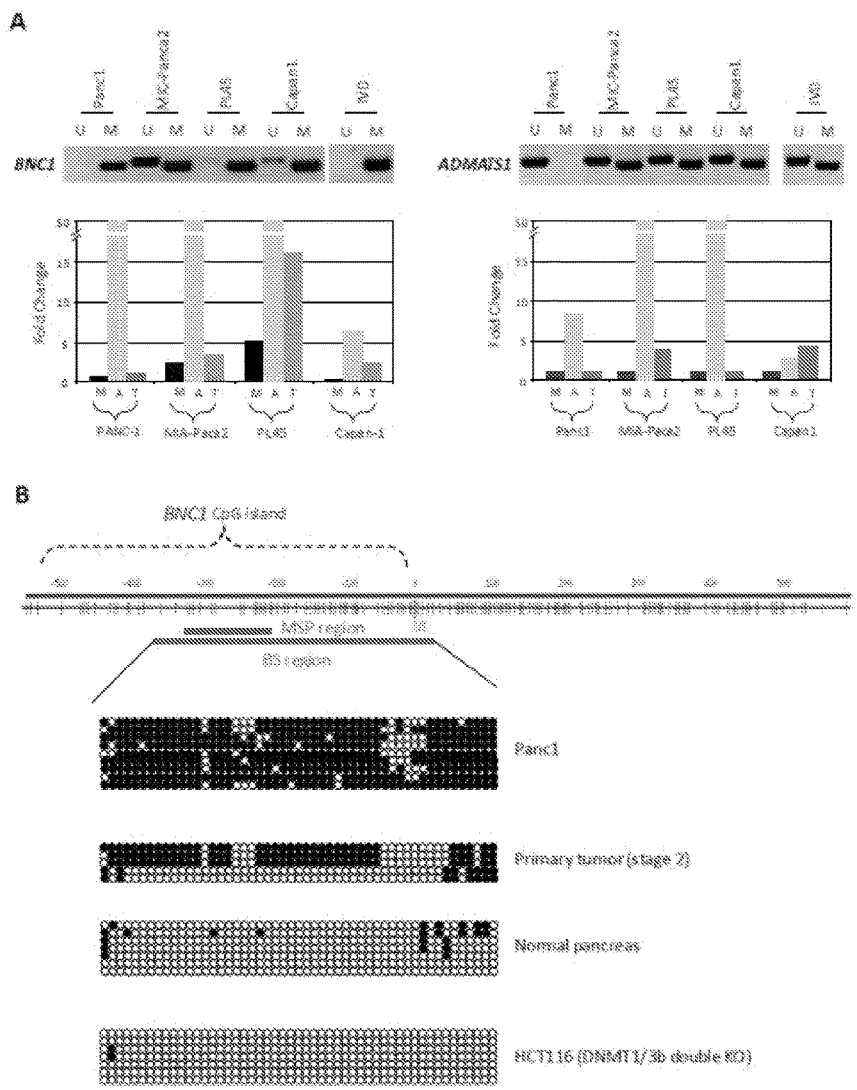
FIGS. 2A, 2B, and 2C depict promoter methylation gels and corresponding bar graphs, a CpG methylation diagram, and a schematic depicting methylation-on-bead (MOB) technology, respectively.

This genome-wide DNA hypermethylome screening is based on a pharmacological approach using 5-deoxy-azacytidineand TSA, which has shown an excellent correlation between promoter DNA methylation and inhibition of gene expression and re-expression after treatment with a DNA demethylating drug, such as 5-deoxy-azacytidine, in prior studies on breast and colorectal cancer. Here, promoter methylation of BNC1 and ADAMTS1 was tested, and correlated with a lack of gene expression in pancreatic cancer cell lines (Panc1, MIA-PaCa2, Capan1, and PL45) using quantitative RT-PCR (qRT-PCR) (FIG. 2A, upper panel). Both genes showed virtually undetectable (or no/low) endogenous gene expression, and significant re-expression after 5-deoxy-azacytidine treatment. As shown in FIG. 2A, lower panel, treatment with a histone deacetylase inhibitor, such as TSA, resulted in minimal re-expression, except in the case of PL45, which may be regulated both by promoter DNA methylation and histone modifications. Promoter-associated CpG island methylation in the BNC1 promoter was detected by bisulfite sequencing analysis in pancreatic cancer cell line (Panc1), a primary pancreas cancer sample (stage 2), and normal pancreatic tissue. As shown in FIG. 2B, bisulfite sequencing analysis showed dense methylation in the pancreatic cancer cell line and the primary pancreatic cancer and minimal/no methylation in normal pancreas samples consistent with the methylation specific PCR analysis.

Figure 2C:
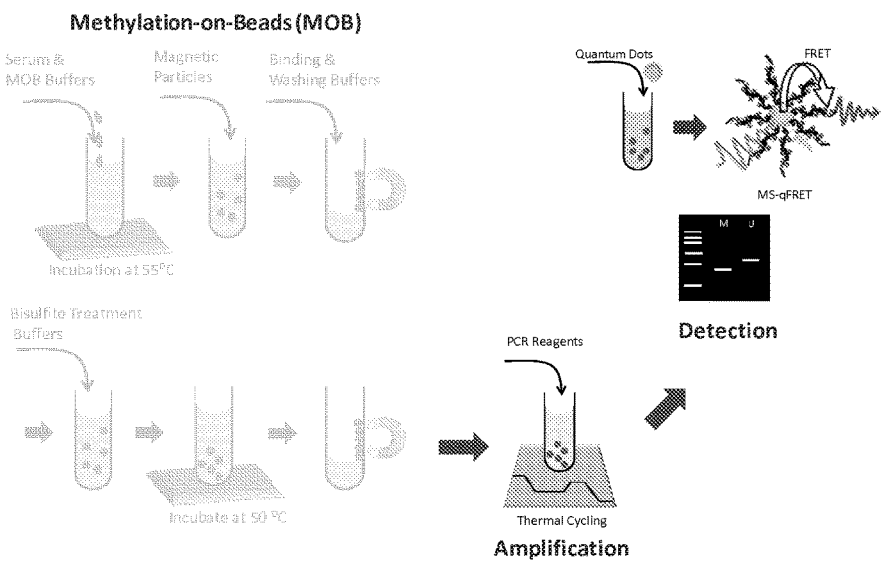

Example 3: Detection of DNA Methylation in Pancreatic Cancer Patient Sera Using Methylation on Beads Technology Early detection of disease results in an improved clinical outcome for most types of cancer. This is particularly relevant for pancreatic cancer, which is poorly accessible and difficult to diagnose. Consequently, 90% of patients with pancreatic cancer present with metastatic or advanced regional disease. Based on the methylation studies, BNC1 and ADAMTS1 have emerged as important biomarkers for the early detection of pancreatic cancer. To determine whether BNC1 and ADMTS1 promoter DNA methylation could be detected in pancreatic cancer patient sera, a highly-sensitive nanoenabled assay, termed methylation on Beads was used, which was developed to improve sensitivity of methylation detection (see, e.g., FIG. 2C). To test the utility of methylation on beads as a tool for early detection of pancreatic cancers, serum samples from a series of pancreatic cancer patients (n=42; stages 1-4), as well as a panel of normal healthy serum samples (n=26) was tested. Sensitivity was determined based on the assumption that all patients with cancer would be methylated for both genes, while all healthy normal volunteers would be unmethylated for both genes. Methylation was analyzed in 42 serum samples from pancreatic cancer patients and 26 normal volunteers. 33 of the 42 pancreatic cancer patients showed methylation for BNC1, while 20 of the 42 showed methylation for ADAMTS1 (see Table 2).

Overall, for all stages included, the sensitivity for BNC1 and ADAMTS1 was determined to be 78.6% and 47.6%, respectively. Sensitivity of detection of stage I pancreatic cancers was 90% for both genes. Amongst the 26 normal serum samples, 3 of the normal volunteers showed methylation for BNC1 while 2 showed methylation for ADAMTS1. Specificity of detection was determined to be 88.4% for BNC1 and 92.4% for ADAMTS1. Computed results have been presented using a 95% confidence interval and are presented in detail in Table 2. Results in the corresponding tumor were higher for both genes, with 100% sensitivity and specificity for BNC1 and 79.2% sensitivity and 100% specificity for ADAMTS1.

Additionally, the sensitivity and specificity of BNC1 and ADAMTS1 was also tested in other types of cancer, including both colon cancer and lung cancer (Table 2). This data showed that BNC1 was also a useful biomarker for the detection of early stages of colon cancer. For example, BNC1 showed a sensitivity of 84.6% (n=11/13) for stage 1 colon cancers and advanced adenomas. Similarly, BNC1 also showed good sensitivity for the detection of early stage lung cancer as stage 1 lung cancer was detected with a sensitivity of 75% (n=12/16).

TABLE 2

Sensitivity and specificity of BNC1 and ADAMTS1 genes in various cancer patient sera samples

| | | BNC1 | | ADAMTS1 | |
| --- | --- | --- | --- | --- | --- |
| | | Sensitivity(%) | | | |
| Cancer Types: | | Estimated Value | 95% CI | Estimated Value | 95% CI |
| Pancreatic Cancer | | | | | |
| Stage | N | | | | |
| I | 10 | 90.0% (9/10) | | 90.0% (9/10) | |
| II-IV | 32 | 75.0% (24/32) | | 34.4% (11/32) | |
| Total | 42 | 78.6% (33/42) | 60-90% | 47.6% (20/42) | 40-70% |
| Colon Cancer | | | | | |
| Stage | | | | | |
| Adenomas, stage I | 13 | 84.6% (11/13) | | 61.5% (8/13) | |
| II-III | 15 | 66.7% (10/15) | | 73.3% (11/15) | |
| Other cancer* | 2 | 100.0% (2/2) | | 50.0% (1/2) | |
| Total | 30 | 76.7% (23/30) | 70-90% | 66.7% (20/30) | 40-70% |

TABLE 2-continued

Sensitivity and specificity of BNC1 and ADAMTS1 genes in various cancer patient sera samples

| | | BNC1 | | ADAMTS1 | |
|---|---|---|---|---|---|
| | | Sensitivity(%) | | | |
| Cancer Types: | | Estimated Value | 95% CI | Estimated Value | 95% CI |
| Lung Cancer | | | | | |
| Stage | | | | | |
| I | 16 | 75.0% (12/16) | | 62.5% (10/16) | |
| II-III | 4 | 100.0% (4/4) | | 100.0% (4/4) | |
| Total | 20 | 80.0% (16/20) | 60-90% | 70.0% (14/20) | 50-90% |
| Normal | | | | | |
| Specificity | 26 | 88.4% | 70-90% | 92.4% | 70-90% |

CI: Confidential Interval.
*other colorectal malignancies.

Figure 3:
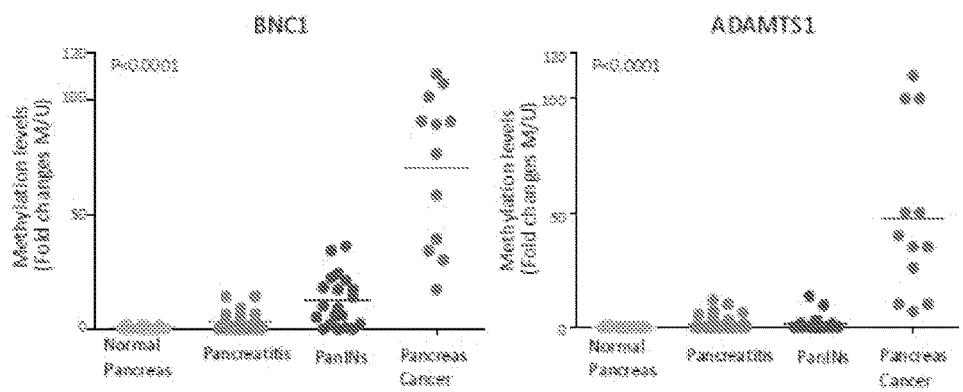
FIG. 3 depicts plots showing the results of quantitative MSP (qMSP) analysis of BNC1 and ADAMTS1 using real-time PCR.

A subset of tissue samples from patients diagnosed with non-cancerous pancreatic diseases, such as pancreatitis, was collected and analyzed. Patients with chronic pancreatitis maybe at increased risk for pancreatic cancer and amongst patients with pancreatic cancer, 5% or more of patients have underlying chronic pancreatitis. Chronic inflammatory conditions likely increases the frequency of methylation as a field defect which may then increase risk of subsequent malignancy. The methylation of BNC1 and ADMATS1 DNA was compared between different conditions (normal, pancreatitis, PanIN, and invasive cancers) using quantitative methylation specific PCR analysis. As shown in FIG. 3, BNC1 and ADAMTS1 showed statistically increased frequency of methylation when comparing normal pancreas tissues and invasive cancers (p<0.0001; both BNC1 and ADAMTS1), as well as chronic pancreatitis and invasive cancers (p<0.0001, both BNC1 and ADAMTS1). There was a low frequency of BNC1 and ADAMTS1 methylation present in non-cancerous disease, such as pancreatitis. More interestingly, there was a significant quantitative difference between PanINs and invasive cancers on both genes (p<0.001 both BNC1 and ADAMTS1). However, BNC1 methylation could be detected in the earliest stages of pancreatic carcinogenesis such as PanIN's, compared to ADAMTS1 methylation (see FIG. 3), indicating that BNC1 methylation is a very early event, and that ADMATS1 methylation is a later event during pancreas cancer development.

Example 4: Tumor Suppressive Effects of BNC1 Gene Over-Expression in Pancreatic Cancer Cells According to the methylation data in pancreatic cancer patients, BNC1 is a useful DNA methylation biomarker in pancreatic cancer patients. To determine whether BNC1 played a role as a tumor suppressor in pancreatic cancer cells, in vitro colony formation assays were performed to determine the effects of full-length BNC1 transfected into Panc1 and MIA-PaCa2 cells lacking BNC1 expression. Compared with control cells transfected with empty vector, over-expression of a full-length BNC1 gene induced a nearly 2.2-fold (Panc1) and 9-fold (MIA-PaCa2) reduction of G418-resistant colonies (see FIG. 4A). In addition, there was a 75% (Panc1) and 81% (MIA-PaCa2) decrease in cell proliferation as measured by [$^3$H] thymidine activity (FIGS. 4B and 4C; left and middle panel). However, overexpression of BNC1 gene had no effect on Panc1 and MIA-PaCa2 cells migration and invasion through matrigel-coated transwell membranes compared with control cells transfected with empty vector (FIGS. 4B and 4C; right panel). Taken together, these data indicated that BNC1 gene has tumor-suppressive effects in human pancreatic cancer cells.

In this study, genome-wide gene expression profiling using a pharmacological approach (5-deoxy-azacytidine and TSA) was used in pancreatic cancer cell lines, a platform which has been used to identify an early detection marker for colorectal cancer. Defining the DNA hypermethylome has been useful as it has allowed the identification of not only novel DNA methylation biomarker candidates, but also of tumor suppressor gene candidates in many types of cancers (colon, breast, ovarian, etc). The identified DNA methylation biomarkers will facilitate diagnostics, and also contribute to therapeutics as predictors of response to therapy.

The poor accessibility of the pancreas along with the late presentation of symptoms has thwarted attempts at timely detection of malignancy, and contributed to the high mortality rates of pancreatic cancer, which is the fourth leading cause of cancer death in both men and women. Therefore, the development of cancer biomarkers of pancreatic cancer is the best hope for early detection.

As reported herein above, the promoter methylation of BNC1 and ADAMTS1 is an excellent early detection biomarker for pancreatic cancer. BNC1 and ADAMTS1 have not been described as a DNA methylation biomarker in pancreatic cancers, although they have been reported methylated in lung cancers.

Screening with a nanobased high sensitive technology allowed the sensitive and specific detection of pancreatic cancer in its earliest stages. Using BNC1 and ADAMTS1, provided for the detection of very early stages of pancreatic carcinoma, with an overall sensitivity of 83.7% (95% CI; 74.2-90.3%) and a specificity of 84.6% (95% CI; 64.3-95.0%). Significantly, the sensitivity achieved in this study is higher than previously reported for serum hypermethylation markers. The present invention provides a cost-effective approach for screening individuals identified as having risk factors for pancreatic cancer in the general population. Additionally, the nano-based methylation on beads detection method significantly reduced the quantity of serum necessary for analysis. The invention provides a paradigm for widespread screening for pancreatic cancers using a simple blood test.

In conclusion, this is the first study to describe the utility of BNC1 and ADAMTS1 promoter methylation as biomarkers in pancreatic cancer patient serum using nanoparticle-enabled technology. In addition, this is the first report to demonstrate a tumor suppressor role for BNC1 in pancreatic cancer. These data indicate that BNC1 promoter methylation is useful as a sensitive and specific noninvasive pre-selection modality for diagnosing subjects as having cancer and identifying individuals at risk for pancreatic cancer.

The results presented hereinabove were carried out using the following methods and materials.

Gene Expression Microarray Analysis

Total RNA was harvested from log phase cells using standard methods (e.g. with TRIzol (Invitrogen™) and the RNeasy kit (Qiagen™) according to the manufacturer's instructions), including a DNase digestion step. RNA was quantified using a spectrophotometer (e.g. the NanoDrop™ ND-100 (http://www.nanodrop.com/)) followed by quality assessment with a microfluidics analysis platform (e.g. the Agilent™ 2100 Bioanalyzer (Agilent Technologies, http://www.agilent.com/). RNA concentrations for individual samples were greater than 200 ng/ll, with 28S/18S ratios greater than 2.2 and RNA integrity of 10 (10 scored as the highest). Sample amplification and labeling procedures were carried out using standard methods (e.g. Low RNA Input Fluorescent Linear Amplification Kit (Agilent Technologies™) according to the manufacturer's instructions). The labeled cRNA was purified using spin columns (e.g. the RNeasy mini kit (Qiagen™)) and quantified. RNA spike-in controls (Agilent Technologies™) were added to RNA samples before amplification. Samples (0.75 lg) labeled with Cy3 or Cy5 were mixed with control targets (Agilent Technologies™), assembled on Oligo Microarray, hybridized, and processed according to the Agilent microarray protocol. Scanning was performed with a microarray scanner (Agilent™ G2565BA, using recommended settings). Data analysis was conducted as previously reported (Schuebel K, Chen W, Cope L, Glöckner S C, Suzuki H, et al., Comparing the DNA hypermethylome with gene mutations in human colorectal cancer. 2007, PLOS Genetics, 3(9):1709-1723.

Patient Samples and Study Population

Patient samples were prepared from formalin-fixed, paraffin-embedded (FFPE) tissue samples from patients with pancreatic cancer procured from the pathology archives of the Johns Hopkins Hospital in accordance with all rules and regulations of the Institutional Review Board (IRB) and as per HIPAA compliance. A total of 167 patients were analyzed in the current study. The Johns Hopkins cohort consisted of 143 tissue samples from pancreatic cancer patients with stage 1 through stage 4 disease who underwent primary surgery and other treatment for pancreatic cancer at the JHH from 1998 to 2009 (Median follow up of 6.4 years). Patients in this cohort were similar by stage with respect to gender, proportion of cases with lymphovascular invasion, and pathologic grade (Table 1). An additional 20 FFPE tissue samples were obtained from patients who had undergone surgical resection but diagnosed with precancerous lesions, pancreatic intraepithelial neoplasias (PanINs). Finally, 4 FFPE tissue samples were obtained from pathology archives from patients who had undergone pancreatic resection with no abnormality noted on gross or microscopic examination.

Pancreatic Cancer Patient Serum Samples

Patient serum samples were obtained from individuals with pancreatic cancer prior to undergoing surgical treatment at the JHH after obtaining informed consent from 2007 to 2009. Matching tumor samples were drawn from the pathology archives of the Johns Hopkins Hospital in accordance with all rules and regulations of the Institutional Review Board (IRB) and as per HIPAA compliance. A total of 36 serum samples were tested, 23 of which had matching FFPE tissue available. Patient serum samples were also obtained from individuals with pancreas (42 samples, Stages 1-4), colon (30 samples, Stages 1-3 and adenomas) and lung cancers (20 samples, Stages 1-3) prior to undergoing surgical treatment at the JHH after obtaining informed consent. Additionally, 26 serum samples were obtained from normal, healthy volunteers to serve as controls.

Cell Culture and Treatment

Cancer cell lines (Pancreas cancer cell lines; Panc1, MIA-PaCa2, PL45, Capan1, Bxpc3, Capan2, PK9, Aspc 1, PK8, and PL3) were obtained from ATCC and cultured in appropriate media and under conditions described by ATCC, with media obtained from InVitrogen™ supplemented with 10% fetal bovine serum (Gemini Bio-Products) and 1% penicillin/streptomycin (InVitrogen™). DKO cells (HCT116 colon cancer cells with genetic disruption of DNMT1 and DNMT3b) were cultured as described previously (Rhee et al., 2002, Nature).

DNA Methylation Analyses and RT-PCR for Expression Analysis

Primer pairs were preferentially designed near the putative transcriptional start site (TSS) in the 5' CpG islands of the genes. Primer sequences for methylation specific PCR analysis were designed using MSPPrimer (http://www.m-spprimer.org). All primer sequences are listed in Table 3. For expression studies using RT-PCR, primers were designed using the open access program Primer3 (http://frodo.wi.m-it.edu/cgi-bin/primer3/primer3 www.cgi).

TABLE 3

Primers used for MSP, RT-PCR, Bisulfite sequencing analyses

| Genes | Primers | S(5-3) | SEQ ID NO | AS(5-3) | SEQ ID NO |
|---|---|---|---|---|---|
| ADAMTS1 | Unmeth | tTATTGtAAAGttAGGGTGtGtTAttGGAtG | 7 | aaaaCTaAaaCAACaCaaAaATTaaTaCCTaaCa | 8 |
|  | Meth | ttAGGGTGCGtTAtCGGAC | 9 | TaAaaCAACGCGaAaATTaaTaCCTaaCG | 10 |
|  | RT | tcgaagtgaaacagcggaac | 11 | gccgctgtacctcaagacaa | 12 |
| ASCL2 | Unmeth | tGtTAGGGGAtAGtGtGtttAGtttAGtTGtG | 13 | CaTACaCaTaaCaCaTaaCTCACaaaaAaCATCa | 14 |
|  | Meth | GAtAGCGCGtttAGtttAGtTCGC | 15 | TaaCGCGTaaCTCACGaaaAaCATCG | 16 |
| BNC1 | Unmeth | TTtGtttTTUttGGGAGAGGtAAAtAttGAtAtG | 17 | aaAaACCTCaCCaaCaaCCaaCa | 18 |
|  | Meth | GtttTTtttCGGGAGAGGtAAAtAtCGAtAC | 19 | CCGaCGaCCGaCG | 20 |
|  | RT | acaaaagcctggcctcatct | 21 | tcgccccaaatgatatgaaa | 22 |
|  | Bisulfite Sequencing | AATtATtTtttTGAGAAGAGYGttAGAGAAtT | 23 | CCCAAaCRCCCAaaCTaC | 24 |

TABLE 3-continued

Primers used for MSP, RT-PCR, Bisulfite sequencing analyses

| Genes | Primers | S(5-3) | SEQ ID NO | AS(5-3) | SEQ ID NO |
|---|---|---|---|---|---|
| BNIP3 | Unmeth | ttAtGttttTGtGtAtGtGtAGGttttAAGTtGtG | 25 | aCTCCCaaACTaAaCaaAaCCCCa | 26 |
| | Meth | GtACGCGtAGGttttAAGTCGC | 27 | CCGaACTaAaCGaAaCCCCG | 28 |
| EVL | Unmeth | GTGTGTTTTTTTTTGAGGATTTGGAGTTGTTTG | 29 | ACCACCAAAAAATAAAAAAACAAAAAACAAACCA | 30 |
| | Meth | GAGGATTCGGAGTCGTTC | 31 | CCGAAAAATAAAAAAACGAAAAACGAACCG | 32 |
| PNMT | Unmeth | TGGGGGAtGATTGttGtTGtAGttG | 33 | CaCCaAaCCaCCCaaaaCCATaTaCa | 34 |
| | Meth | GGGGACGATTGtCGtTGtAGtC | 35 | AaCCGCCCGaaaCCATaTaCG | 36 |
| TFPI2 | Unmeth | CCCACATAAAACAAACACCCAAACCA | 37 | TGGTTTGTTGGGTAAGGTGTTTG | 38 |
| | Meth | GTTCGTTGGGTAAGGCGTTC | 39 | CATAAAACGAACACCCGAACCG | 40 |
| TWIST1 | Unmeth | tAGAtAttTtGtGGGtTtTGtAGtAttGGtAttG | 41 | aCaaaAaaaaaAaaaaACaaTaTaaATaaCCCCa | 42 |
| | Meth | CGGGtTtTGtAGtAtCGGtAtC | 43 | CGAaAaaaaaAaaaaACGaTaTaaATaaCCCCG | 44 |

For methylation-specific PCR analysis, DNA was extracted using the standard phenol-chloroform extraction method. Bisulfite modification of genomic DNA was carried out using standard protocols (e.g. with the EZ DNA methylation Kit (Zymo Research™)). Methylation analysis of CAN gene (Cancer gene, as defined by Wood L D, Parsons D W, Jones S et al., The genomic landscapes of human breast and colorectal cancers, Science. 2007, 318(5853):1108-1113.) promoters was performed using MSP primer pairs located close to the putative transcriptional start site in the 5' CpG island with 2 μl of bisulfite-treated DNA as template and JumpStart Red Taq DNA Polymerase (Sigma™) for amplification as previously described (Herman J G, Graff J R, Myöhänen S, Nelkin B D, Baylin S B., Methylation-specific PCR: a novel PCR assay for methylation status of CpG islands. Proc Natl Acad Sci USA. 1996 Sep. 3; 93(18): 9821-9826).

Total RNA was extracted from cell lines using standard methods (e.g. the RNeasy Mini Kit (Qiagen™)), and treated with DNase. For reverse transcription (RT) reaction, 1 μg of total RNA was subjected to the first strand cDNA synthesis using standard cDNA synthesis protocols (e.g. Superscript III first strand cDNA synthesis kit (InVitrogen™) used according to the manufacturer's instructions). Expression analysis was performed by RT-PCR using 1 μl of cDNA as template and standard amplification protocols (e.g. JumpStart Red Taq DNA Polymerase (Sigma™)).

Quantitative Methylation-Specific PCR Using Real-Time PCR

Sodium bisulfite modification, which converts unmethylated cytosine residues to uracil residues, was first carried out on 1 ug genomic DNA isolated from the paraffin-embedded tissue sections using standard methylation procedures (e.g. EZ DNA methylation kit (Zymo Research Co) according to the manufacturer's instructions). For quantitative real-time analyses, standard procedures were used. For example, the Power SYBR Green PCR kit (Applied Biosystems) was used and the amplification conditions consisted of an initial 10 minute denaturation step at 95° C., followed by 40 cycles of denaturation at 95° C. for 15 seconds and annealing and extension for 30 seconds and 60 seconds, respectively. An ABI StepOnePlusReal-Time PCR System was used (Applied Biosystems), and for quantification the comparative cycle threshold (Ct) method was used, normalizing the Ct values for the indicated gene to the Ct values of Unmethylated reaction relative to a methylated reaction sample.

Methylation on Beads (MOB) Method

Methods and buffers used for methylation on beads extraction are as described previously (Bailey V J, Zhang Y, Keeley B P, Yin C, Pelosky K L, Brock M, Baylin S B, Herman J G, Wang T H. Single-tube analysis of DNA methylation with silica superparamagnetic beads. Clin Chem. 56(6):1022-1025). Briefly, 50 μL of Protease K was added into the bottom of an eppendorf tube, and 200 μL methylation on beads Binding Buffer 1 and 100 μL Lysing Buffer to 200 μL was added to the serum sample. The sample was incubated at 55° C. for 15 minutes (cell lines, whole blood), and 200 μL 100% Isopropyl Alcohol was added, and the sample was mixed. 35 μL of Magnetic Beads was then added to the sample and mixed. The tube was then placed on the magnetic holder to capture the beads, and the supernatant was discarded. The tube was removed from the magnetic holder, and the beads were washed with 500 μL of Wash Buffer 1. The beads were once again captured on the magnetic holder, and then washed a second time in 500 μL of Wash buffer 2. This step was then repeated one time, and the beads were again captured, and the supernatant was discarded. 50 μL of Elution Buffer was added to the eppendorf tube containing the washed beads. To denature the DNA for bisulfite treatment, 6 μL 2M NaOH was added to the tube, mixed, and incubated at 70° C. for 10-15 minutes. 12 μL of freshly prepared hydroquinone solution was then added and mixed. 200 μL of prepared NaBisulfite solution was added and mixed. The NaBisulfite solution was vortexed to insure that it was fully saturated. The sample was incubated at 65° C. for 4-6 hours, and then 120 μL of 10M NaOH was added, mixed, and incubated at 50° C. for an additional 10 minutes. 350 μL of methylation on beads Binding Buffer 2, 100 μL of IPA was added to the sample and mixed. The beads were then captured and washed once in Wash Buffer 1 and twice in Wash Buffer 2 as described above. The beads were then captured and the supernatant discarded. The DNA was then eluted from the magnetic beads with 100 μL of PCR buffer. The sample was then divided as desired for subsequent PCR amplification.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of identifying and treating a subject, the method comprising:
   (a) obtaining a biological sample from the subject;
   (b) isolating genomic DNA from the biological sample;
   (c) bisulfite treating the genomic DNA;
   (d) PCR amplifying the bisulfite-treated genomic DNA to obtain one or more PCR products;
   (e) hybridizing the one or more PCR products to a fluorescently labeled oligonucleotide comprising SEQ ID NOS: 19 or 20 for detection of methylated nucleotides of the BNC1 gene promoter or exon 1, thereby forming a first PCR product-fluorescently labeled oligonucleotide probe complex;
   (f) hybridizing the one or more PCR products to a fluorescently labeled oligonucleotide comprising SEQ ID NOS: 9 or 10 for detection of methylated nucleotides of the ADAMTS1 gene promoter or exon 1, thereby forming a second PCR product-fluorescently labeled oligonucleotide probe complex; and
   (g) detecting an elevated level of the first PCR product fluorescently labeled oligonucleotide complex as compared to a first reference level obtained in a sample previously obtained from the subject and detecting an elevated level of the second PCR product-fluorescently labeled oligonucleotide complex relative to a second reference level obtained in a sample previously obtained from the subject, and (h) administering an epigenetic therapy or resecting the pancreas of the subject having an elevated level of the first and second PCR products detected in step (g), wherein the epigenetic therapy is selected from the group consisting of entinostat, SAHA (suberovlanilide hydroxamic acid), depsipeptide, azocvtidine, and deazocytidine.

2. The method of claim 1, further comprising detecting an alteration in the sequence or expression level of a Brca1, Brca2, p16, K-ras, APC, EGFR, and/or EML-ALK4 gene or polypeptide.

3. The method of claim 1, wherein the biologic sample is a tissue or biologic fluid sample.

4. The method of claim 1, wherein the biologic sample is selected from the group consisting of blood, serum, plasma, urine, pancreatic juice, pancreatic cyst fluid, or lung lavage.

5. The method of claim 1, wherein the methylation levels of the BNC1 and ADAMTS1 promoters are quantified.

6. The method of claim 1, wherein the subject is a smoker, has a Brca1 or Brca2 mutation, pancreatic cyst, chronic pancreatitis, presence of colon polyps or adenomas, or a family history of cancer.

7. A method for diagnosing and treating pancreatic cancer in a subject comprising:
   a) detecting methylated nucleotides of the BNC1 gene promoter or exon 1 using an oligonucleotide comprising SEQ ID NO: 19;
   b) detecting methylated nucleotides of the ADAMTS1 gene promoter or exon 1 using an oligonucleotide comprising SEQ ID NO: 9;
   c) detecting an elevated level of methylated nucleotides in both BNC1 and ADAMTS1 gene promoters or exon 1 nucleotides as compared to a reference level;
   d) diagnosing the subject as having pancreatic cancer; and
   e) administering an epigenetic therapy or resecting the pancreas of the patient diagnosed as having pancreatic cancer.

8. The method of claim 7, wherein the epigenetic therapy comprises an therapeutically effective amount of histone deacetylase or methylation inhibitors.

* * * * *